United States Patent

(12) United States Patent
Qu et al.

(10) Patent No.: US 8,052,899 B2
(45) Date of Patent: Nov. 8, 2011

(54) HEPTARYLENE- AND OCTARYLENETETRACARBOXIMIDES AND PREPARATION THEREOF

(75) Inventors: Jianqiang Qu, Ludwigshafen (DE); Neil Gregory Pschirer, Mainz (DE); Martin Koenemann, Mannheim (DE); Klaus Muellen, Cologne (DE); Yuri Avlasevic, Mainz (DE)

(73) Assignees: BASF Aktiengesellschaft, Ludwigshafen (DE); Max-Planck-Gesellschaft zur Förderung der Wissenschaften e.V., München (DE)

( * ) Notice: Subject to any disclaimer, the term of this patent is extended or adjusted under 35 U.S.C. 154(b) by 42 days.

(21) Appl. No.: 12/513,410

(22) PCT Filed: Oct. 25, 2007

(86) PCT No.: PCT/EP2007/061457
§ 371 (c)(1),
(2), (4) Date: May 4, 2009

(87) PCT Pub. No.: WO2008/052927
PCT Pub. Date: May 8, 2008

(65) Prior Publication Data
US 2010/0072438 A1   Mar. 25, 2010

(30) Foreign Application Priority Data
Nov. 2, 2006   (EP) .................................... 06123380

(51) Int. Cl.
| | |
|---|---|
| F21V 9/04 | (2006.01) |
| F21V 9/06 | (2006.01) |
| G02B 5/22 | (2006.01) |
| G02B 5/26 | (2006.01) |
| C07D 221/18 | (2006.01) |
| C07D 221/22 | (2006.01) |

(52) U.S. Cl. ................... 252/587; 252/301.16; 252/700; 546/26; 546/27; 524/90; 106/499

(58) Field of Classification Search .................. 252/587, 252/301.16, 700; 524/90, 91, 89; 546/26, 546/27, 37, 100, 28, 38; 106/499, 31.47, 106/31.2, 31.32; 257/40, E51.024; 549/232; 8/636

See application file for complete search history.

(56) References Cited

U.S. PATENT DOCUMENTS
| | | | |
|---|---|---|---|
| 6,890,377 B2 | 5/2005 | Boehm et al. | |
| 7,408,061 B2 | 8/2008 | Krieger et al. | |
| 2008/0188660 A1 | 8/2008 | Pschirer et al. | |
| 2009/0236591 A1 | 9/2009 | Konemann et al. | |

FOREIGN PATENT DOCUMENTS
| | | |
|---|---|---|
| WO | 02 068538 | 9/2002 |
| WO | 02 077081 | 10/2002 |
| WO | 2004 026965 | 4/2004 |
| WO | 2006 111511 | 10/2006 |

OTHER PUBLICATIONS

U.S. Appl. No. 12/673,908, filed Feb. 17, 2010, Koenemann et al.
U.S. Appl. No. 12/666,127, filed Dec. 22, 2009, Koenemann et al.
U.S. Appl. No. 12/479,228, filed Jun. 5, 2009, Koenemann et al.
U.S. Appl. No. 12/668,975, filed Jan. 13, 2010, Pschirer et al.
U.S. Appl. No. 12/738,947, filed Apr. 20, 2010, Koenemann et al.
U.S. Appl. No. 13/119,192, filed Mar. 16, 2011, Koenemann et al.
Pschirer, Neil G. et al., "Pentarylene- and Hexarylenebis(dicarboximide)s: Near-Infrared-Absorbing Polyaromatic Dyes", Angew. Chem. Int., Ed. 45, pp. 1401-1404, (2006).

*Primary Examiner* — Ling Choi
*Assistant Examiner* — Bijan Ahvazi
(74) *Attorney, Agent, or Firm* — Oblon, Spivak McClelland, Maier & Neustadt, L.L.P.

(57) ABSTRACT

The present invention relates to heptarylene- and octarylene-tetracarboximides of the general formula (I)

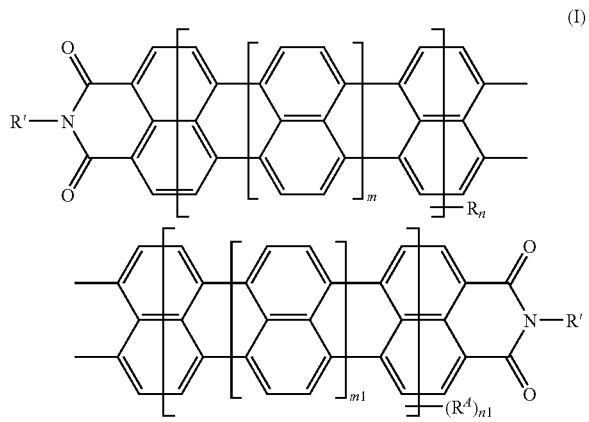

(I)

to precursors thereof or mixtures thereof, and to processes for their preparation and to their use.

25 Claims, No Drawings

HEPTARYLENE- AND OCTARYLENETETRACARBOXIMIDES AND PREPARATION THEREOF

This application is a 371 of PCT/EP07/61457, filed Oct. 25, 2007.

The present invention relates to heptarylene- and octarylenetetracarboximides, and to their preparation and use.

Rylenetetracarboximides are known to be of particular interest from an application point of view owing to their strong absorption in the near infrared (NIR) region of the electromagnetic spectrum.

For example, WO-A 02/77081 describes the use of quaterrylenetetracarboximides as infrared absorbers for heat protection in glass laminates.

Pentarylene- and hexarylene derivatives which are unsubstituted or have a low degree of substitution are described by N. G. Pschirer et al., Angew. Chem. Int. Ed. 45 (2006), 1401-1404.

Similar pentarylene- and hexarylene derivatives are also described in DE-A 10 2005 018241.

In spite of the pentarylene and hexarylene derivatives already described and their use in connection with their absorption capacity in the NIR, there is a need for further higher, especially highly substituted, derivatives, and for processes for their preparation.

It is thus an object of the present invention to provide such derivatives and processes for their preparation, which are of particular interest especially owing to their absorption capacity and should be easy to prepare owing to very simple preparation processes in spite of their comparatively high molecular weight and, if appropriate, high degree of substitution.

This object is achieved by a process for preparing heptarylene- and octarylenetetracarboximides, comprising the steps of (a) coupling at least one quaterrylene compound of the formula (II)

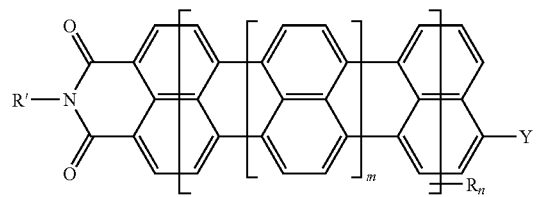

(II)

with at least one compound of the formula (III)

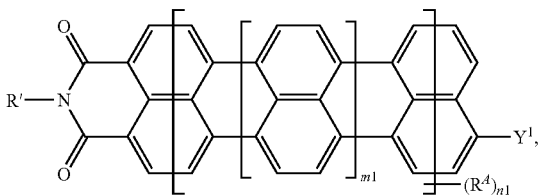

(III)

where

Y, $Y^1$ are each halogen, or one radical of Y, $Y^1$ is halogen and the other is $B(OR'')_2$;

each R, $R^A$ are independently identical or different radicals selected from the following:

aryloxy, arylthio, hetaryloxy or hetarylthio, to each of which may be fused further saturated or unsaturated 5- to 7-membered rings whose carbon skeleton may be interrupted by one or more —O—, —S—, —$NR^1$—, —N=$CR^1$—, —CO—, —SO— and/or —$SO_2$— moieties, where the entire ring system may be mono- or polysubstituted by the (i), (ii), (iii), (iv) and/or (v) radicals:

(i) $C_1$-$C_{30}$-alkyl whose carbon chain may be interrupted by one or more —O—, —S—, —$NR^1$—, —N=$CR^1$—, —C≡C—, —$CR^1$=$CR^1$—, —CO—, —SO— and/or —$SO_2$— moieties and which may be mono- or polysubstituted by: $C_1$-$C_{12}$-alkoxy, $C_1$-$C_6$-alkylthio, —C≡$CR^1$, —$CR^1$=$CR^1_2$, hydroxyl, mercapto, halogen, cyano, nitro, —$NR^2R^3$, —$NR^2COR^3$, —$CONR^2R^3$, —$SO_2NR^2R^3$, —$COOR^2$, —$SO_3R^2$, —$PR^2R^3$, —$POR^2R^3$, aryl and/or saturated or unsaturated $C_4$-$C_7$-cycloalkyl whose carbon skeleton may be interrupted by one or more —O—, —S—, —$NR^1$—, —N=$CR^1$—, —$CR^1$=$CR^1$—, —CO—, —SO— and/or —$SO_2$— moieties, where the aryl and cycloalkyl radicals may each be mono- or polysubstituted by $C_1$-$C_{18}$-alkyl and/or the above radicals specified as substituents for alkyl;

(ii) $C_3$-$C_8$-cycloalkyl whose carbon skeleton may be interrupted by one or more —O—, —S—, —$NR^1$—, —N=$CR^1$—, —$CR^1$=$CR^1$—, —CO—, —SO— and/or —$SO_2$— moieties and to which may be fused further saturated or unsaturated 5- to 7-membered rings whose carbon skeleton may be interrupted by one or more —O—, —S—, —$NR^1$—, —N=$CR^1$—, —$CR^1$=$CR^1$—, —CO—, —SO— and/or —$SO_2$— moieties, where the entire ring system may be mono- or polysubstituted by: $C_1$-$C_{18}$-alkyl, $C_1$-$C_{12}$-alkoxy, $C_1$-$C_6$-alkylthio, —C≡$CR^1$, —$CR^1$=$CR^1_2$, hydroxyl, mercapto, halogen, cyano, nitro, —$NR^2R^3$, —$NR^2COR^3$, —$CONR^2R^3$, —$SO_2NR^2R^3$, —$COOR^2$, —$SO_3R^2$, —$PR^2R^3$ and/or —$POR^2R^3$;

(iii) aryl or hetaryl to which may be fused further saturated or unsaturated 5- to 7-membered rings whose carbon skeleton may be interrupted by one or more —O—, —S—, —$NR^1$—, —N=$CR^1$—, —$CR^1$=$CR^1$—, —CO—, —SO— and/or —$SO_2$— moieties, where the entire ring system may be mono- or polysubstituted by: $C_1$-$C_{18}$-alkyl, $C_1$-$C_{12}$-alkoxy, $C_1$-$C_6$-alkylthio, —C≡$CR^1$, —$CR^1$=$CR^1_2$, hydroxyl, mercapto, halogen, cyano, nitro, —$NR^2R^3$, —$NR^2COR^3$, —$CONR^2R^3$, —$SO_2NR^2R^3$, —$COOR^2$, —$SO_3R^2$, —$PR^2R^3$, —$POR^2R^3$, aryl and/or hetaryl, each of which may be substituted by $C_1$-$C_{18}$-alkyl, $C_1$-$C_{12}$-alkoxy, hydroxyl, mercapto, halogen, cyano, nitro, —$NR^2R^3$, —$NR^2COR^3$, —$CONR^2R^3$, —$SO_2NR^2R^3$, —$COOR^2$, —$SO_3R^2$, —$PR^2R^3$ and/or —$POR^2R^3$;

(iv) a —U-aryl radical which may be mono- or polysubstituted by the above radicals specified as substituents for the aryl radicals (iii), where U is a —O—, —S—, —$NR^1$—, —CO—, —SO— or —$SO_2$— moiety;

R' is independently hydrogen;

C$_1$-C$_{30}$-alkyl whose carbon chain may be interrupted by one or more —O—, —S—, —NR$^1$—, —N=CR$^1$—, —C≡C—, —CR$^1$=CR$^1$—, —CO—, —SO— and/or —SO$_2$— moieties and which may be mono- or polysubstituted by the (ii), (iii), (iv) and/or (v) radicals specified as substituents for the R radicals;

C$_3$-C$_8$-cycloalkyl to which may be fused further saturated or unsaturated 5- to 7-membered rings whose carbon skeleton may be interrupted by one or more —O—, —S—, —NR$^1$—, —N=CR$^1$—, —CR$^1$=CR$^1$—, —CO—, —SO— and/or —SO$_2$— moieties, where the entire ring system may be substituted by the (i), (ii), (iii), (iv) and/or (v) radicals specified as substituents for the R radicals;

aryl or hetaryl to which may be fused further saturated or unsaturated 5- to 7-membered rings whose carbon skeleton may be interrupted by one or more —O—, —S—, —NR$^1$—, —N=CR$^1$—, —CR$^1$=CR$^1$—, —CO—, —SO— and/or —SO$_2$— moieties, where the entire ring system may be substituted by the (i), (ii), (iii), (iv), (v) radicals specified as substituents for the R radicals, aryl- and/or hetarylazo, each of which may be substituted by C$_1$-C$_{10}$-alkyl, C$_1$-C$_6$-alkoxy and/or cyano;

each R" is independently hydrogen, C$_1$-C$_{30}$-alkyl, C$_5$-C$_8$-cycloalkyl, aryl or hetaryl or are joined together with formation of a 5- to 7-membered ring which comprises the two oxygen atoms and also the boron atom, to which may be fused unsaturated or saturated rings and which may be substituted on the carbon atoms by up to 4 C$_1$-C$_{30}$-alkyl, C$_5$-C$_8$-cycloalkyl, aryl or hetaryl groups;

R$^1$ is hydrogen or C$_1$-C$_{18}$-alkyl, where the R$^1$ radicals may be the same or different when they occur more than once;

R$^2$, R$^3$ are each independently hydrogen;

C$_1$-C$_{18}$-alkyl whose carbon chain may be interrupted by one or more —O—, —S—, —CO—, —SO— and/or —SO$_2$— moieties and which may be mono- or polysubstituted by C$_1$-C$_{12}$-alkoxy, C$_1$-C$_6$-alkylthio, hydroxyl, mercapto, halogen, cyano, nitro and/or —COOR$^1$;

aryl or hetaryl to each of which may be fused further saturated or unsaturated 5- to 7-membered rings whose carbon skeleton may be interrupted by one or more —O—, —S—, —CO— and/or —SO$_2$— moieties, where the entire ring system may be mono- or polysubstituted by C$_1$-C$_{12}$-alkyl and/or the above radicals specified as substituents for alkyl;

and where m, m1, n, n1 fulfill at least one of the following conditions:

m=2, m1=1 and n, n1 are integers whose sum adds up to from 0 to 12;

m=2, m1=2 and n, n1 are integers whose sum adds up to from 0 to 16;

(b) cyclodehydrogenating the reaction product obtained in step (a) to give a rylene compound of the general formula (I)

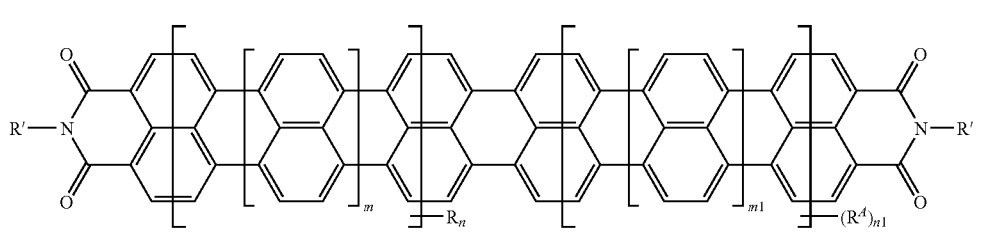

or mixtures thereof.

For the process according to the invention, m, m1, n, n1 fulfill at least one of the following conditions:

To prepare heptarylenetetracarboximides, a corresponding quaterrylene and a corresponding terrylene (m=1, m1=1) are reacted, where n, n1 are integers whose sum adds up to from 0 to 12, i.e. 0, 1, 2, 3, 4, 5, 6, 7, 8, 9, 10, 11 or 12, preferably 4, 5, 6, 7, 8, 9 or 10, in particular 5, 6, 7 or 8. Examples of n+n1 are 8+0, 7+0, 6+0, 5+0, 4+0, 3+0, 2+0, 1+0, 0+0, 8+1, 7+1, 6+1, 5+1, 4+1, 3+1, 2+1, 1+1, 0+1, 8+2, 7+2, 6+2, 5+2, 4+2, 3+2, 2+2, 1+2, 0+2, 8+3, 7+3, 6+3, 5+3, 4+3, 3+3, 2+3, 1+3, 0+3, 8+4, 7+4, 6+4, 5+4, 4+4, 3+4, 2+4, 1+4, 0+4, 7+5, 6+5, 5+5, 4+5, 3+5, 2+5, 1+5, 0+5, 6+6, 5+6, 4+6, 3+6, 2+6, 1+6, 0+6. For n+n1, preference is given to 6+4, 5+4, 4+4, 3+4, 6+3, 5+3, 4+3, 3+3, 6+2, 5+2, 4+2, 3+2, 2+2.

To prepare octarylenetetracarboximides, two corresponding quaterrylenes (m=2, m1=2) are reacted, where n, n1 are integers whose sum adds up to from 0 to 16, i.e. 0, 1, 2, 3, 4, 5, 6, 7, 8, 9, 10, 11, 12, 13, 14, 15 or 16, preferably 4, 5, 6, 7, 8, 9 or 10, more preferably 4, 5, 6, 7 or 8, in particular 5, 6, 7 or 8. Examples of n+n1 are 8+0, 7+0, 6+0, 5+0, 4+0, 3+0, 2+0, 1+0, 0+0, 8+1, 7+1, 6+1, 5+1, 4+1, 3+1, 2+1, 1+1, 0+1, 8+2, 7+2, 6+2, 5+2, 4+2, 3+2, 2+2, 1+2, 0+2, 8+3, 7+3, 6+3, 5+3, 4+3, 3+3, 2+3, 1+3, 0+3, 8+4, 7+4, 6+4, 5+4, 4+4, 3+4, 2+4, 1+4, 0+4, 8+5, 7+5, 6+5, 5+5, 4+5, 3+5, 2+5, 1+5, 0+5, 8+6, 7+6, 6+6, 5+6, 4+6, 3+6, 2+6, 1+6, 0+6, 8+7, 7+7, 6+7, 5+7, 4+7, 3+7, 2+7, 1+7, 0+7, 8+8, 7+8, 6+8, 5+8, 4+8, 3+8, 2+8, 1+8, 0+8. For n+n1, preference is given to 6+6, 6+5, 6+4, 6+3, 5+6, 5+5, 5+4, 5+3, 4+6, 4+5, 4+4, 4+3, 3+6, 3+5, 3+4, 3+3, 2+2.

The object is also achieved by heptarylenetetracarboximides of the general formula (I) or mixtures thereof, where n and n1 are integers whose sum adds up to from 0 to 12, i.e. 0, 1, 2, 3, 4, 5, 6, 7, 8, 9, 10, 11 or 12, preferably 4, 5, 6, 7, 8, 9 or 10, in particular 5, 6, 7 or 8, and R, R$^A$, R', m, m1 are each as defined above. Examples of n+n1 are 8+0, 7+0, 6+0, 5+0, 4+0, 3+0, 2+0, 1+0, 0+0, 8+1, 7+1, 6+1, 5+1, 4+1,3+1, 2+1, 1+1, 0+1, 8+2, 7+2, 6+2, 5+2, 4+2, 3+2, 2+2, 1+2, 0+2, 8+3, 7+3, 6+3, 5+3, 4+3, 3+3, 2+3, 1+3, 0+3, 8+4, 7+4, 6+4, 5+4, 4+4, 3+4, 2+4, 1+4, 0+4, 7+5, 6+5, 5+5, 4+5, 3+5, 2+5, 1+5, 0+5, 6+6, 5+6, 4+6, 3+6, 2+6, 1+6, 0+6. For n+n1, preference is given to 6+4, 5+4, 4+4, 3+4, 6+3, 5+3, 4+3, 3+3, 6+2, 5+2, 4+2, 3+2, 2+2.

The inventive heptarylene compounds can thus be obtained with the aid of the process according to the invention by coupling a corresponding quaterrylene compound to the corresponding terrylene compound. The inventive heptarylene compounds may have a high degree of substitution. However, the sum of the R and $R^A$ substituents is not more than 12.

The object is also achieved by octarylenetetracarboximides of the general formula (!) or mixtures thereof, where n and n1 are integers whose sum adds up to from 0 to 16, i.e. 0, 1, 2, 3, 4, 5, 6, 7, 8, 9, 10, 11, 12, 13, 14, 15 or 16, preferably 4, 5, 6, 7, 8, 9 or 10, more preferably 4, 5, 6, 7 or 8, in particular 5, 6, 7 or 8, and R, $R^A$, R', m, m1 are each as defined above. Examples of n+n1 are 8+0, 7+0, 6+0, 5+0, 4+0, 3+0, 2+0, 1+0, 0+0, 8+1, 7+1, 6+1, 5+1, 4+1, 3+1, 2+1, 1+1, 0+1, 8+2, 7+2, 6+2, 5+2, 4+2, 3+2, 2+2, 1+2, 0+2, 8+3, 7+3, 6+3, 5+3, 4+3, 3+3, 2+3, 1+3, 0+3, 8+4, 7+4, 6+4, 5+4, 4+4, 3+4, 2+4, 1+4, 0+4, 8+5, 7+5, 6+5, 5+5, 4+5, 3+5, 2+5, 1+5, 0+5, 8+6, 7+6, 6+6, 5+6, 4+6, 3+6, 2+6, 1+6, 0+6, 8+7, 7+7, 6+7, 5+7, 4+7, 3+7, 2+7, 1+7, 0+7, 8+8, 7+8, 6+8, 5+8, 4+8, 3+8, 2+8, 1+8, 0+8. For n+n1, preference is given to 6+6, 6+5, 6+4, 6+3, 5+6, 5+5, 5+4, 5+3, 4+6, 4+5, 4+4, 4+3, 3+6, 3+5, 3+4, 3+3, 2+2.

The inventive octarylene compounds can thus be obtained with the aid of the process according to the invention by coupling two corresponding quaterrylene compounds. The inventive octarylene compounds may have a high degree of substitution. However, the sum of the R and $R^A$ substituents is not more than 16.

The starting compounds of the formulae (II), (III), (IIIa) are known from the prior art or can be prepared with the aid of literature syntheses of analogous compounds. Especially terrylene and quaterrylene derivatives which can serve as starting materials for the process according to the invention for preparing heptarylene- and octarylenetetracarboximides, are described in German patent application 10 2005 021362. In addition, the preparation of hexarylene- and pentarylenetetracarboximides is described in DE-A 10 2005 018241. The inventive imide compounds can be prepared analogously.

The process according to the invention for preparing heptarylene- and octarylenetetracarboximides comprises, as the first step (a), the coupling of at least one quaterrylene compound of the formula (II) with at least one compound of the formula (III), where the two units are linked in each case with the aid of the Y and $Y^1$ groups.

In this case, Y and $Y^1$ may be halides, through which the desired bonding of the two aromatic units is enabled with the aid of a catalytic coupling. It is equally possible that one of the Y, $Y^1$ radicals may be a halide and the other may be a boronic acid or a similar compound of the formula $B(OR")_2$. In that case, coupling is effected via the so-called Suzuki reaction. In both cases, the halides are bromide or chloride.

The inventive diimides are prepared with the aid of the process according to the invention preferably in the presence of an organic solvent, if desired in a mixture with water, and of a transition metal catalyst and of a base, and, as has been stated above, one of the two units may be a boronic acid derivative and the other a halide.

Such a boronic acid derivative is obtainable, for example, by reacting the corresponding halogenated aromatic with the aid of diboranes of the general formula (IV) $(R"O)_2B—B(OR")_2$ in the presence of an aprotic organic solvent, of a transition metal catalyst and of a base.

Suitable diboranes of the general formula (IV) are especially bis(1,2- and 1,3-diolato)diboranes, tetraalkoxydiboranes, tetracycloalkoxydiboranes and tetra(het)aryloxydiboranes and their mixed forms. Examples of these compounds include: bis(pinacolato)diborane, bis(1,2-benzodiolato)diborane, bis(2,2-dimethyl-1,3-propanediolato)diborane, bis(1,1,3,3-tetramethyl-1,3-propanediolato)diborane, bis(4,5-pinanediolato)diborane, bis(tetramethoxy)diborane, bis(tetracyclopentoxy)diborane, bis(tetraphenoxy)diborane and bis(4-pyridiyloxy)diborane.

Preference is given to diboranes of the general formula (IV) in which the two R" radicals on a boron atom are joined together with formation of a five-membered or six-membered ring which comprises the two oxygen atoms and the boron atom. Aromatic or saturated, including bicyclic, rings having from 5 to 7 carbon atoms as ring members may also be fused to the five- or six-membered rings formed. All rings or ring systems may be substituted by up to 4 $C_1$-$C_{30}$-alkyl, $C_5$-$C_8$-cycloalkyl, aryl and/or hetaryl radicals; they are preferably substituted by up to 4 $C_1$-$C_4$-alkyl radicals. Examples of these preferred diboranes are the bis(1,2- and 1,3-diolato)diboranes already mentioned above, particular preference being given to bis(pinacolato)diborane.

The molar ratio of diborane of the general formula (IV) to the halogenated aromatic is generally from 0.8:1 to 3:1, especially from 1.5:1 to 2:1.

Suitable solvents are in principle all aprotic solvents which are stable toward bases under the reaction conditions and have a boiling point above the selected reaction temperature, in which the reactants dissolve completely at reaction temperature and the catalysts and bases used at least partially, so that substantially homogeneous reaction conditions are present. It is possible to use either nonpolar aprotic or polar aprotic solvents.

Examples of preferred nonpolar aprotic solvents are solvents which boil at >100° C. from the following groups: aliphatics (especially $C_8$-$C_{18}$-alkanes), unsubstituted, alkyl-substituted and fused cycloaliphatics (especially unsubstituted $C_7$-$C_{10}$-cycloalkanes, $C_6$-$C_8$-cycloalkanes which are substituted by from one to three $C_1$-$C_6$-alkyl groups, polycyclic saturated hydrocarbons having from 10 to 18 carbon atoms), alkyl- and cycloalkyl-substituted aromatics (especially benzene which is substituted by from one to three $C_1$-$C_6$-alkyl groups or one $C_5$-$C_8$-cycloalkyl radical) and fused aromatics which may be alkyl-substituted and/or partly hydrogenated (especially naphthalene which is substituted by from one to four $C_1$-$C_6$-alkyl groups) and mixtures of these solvents.

Examples of particularly preferred solvents include: octane, isooctane, nonane, isononane, decane, isodecane, undecane, dodecane, hexadecane and octadecane, cycloheptane, cyclooctane, methylcyclohexane, dimethylcyclohexane, trimethylcyclohexane, ethylcyclohexane, diethylcyclohexane, propylcyclohexane, isopropylcyclohexane, dipropylcyclohexane, butylcyclohexane, tert-butylcyclohexane, methylcycloheptane and methylcyclooctane, toluene, o-, m- and p-xylene, 1,3,5-trimethylbenzene (mesitylene), 1,2,4- and 1,2,3-trimethylbenzene, ethylbenzene, propylbenzene, isopropylbenzene, butylbenzene, isobutylbenzene, tert-butylbenzene and cyclohexylbenzene; naphthalene, decahydronaphthalene (decalin), 1- and 2-methylnaphthalene and 1- and 2-ethylnaphthalene; combinations of the aforementioned solvents, as can be obtained from the high-boiling, partly or fully hydrogenated fractions of thermal and catalytic cracking processes in crude oil or naphtha processing, for example mixtures of the Exsol® type and alkylbenzene mixtures of the Solvesso® type.

Very particularly preferred solvents are xylene (all isomers), mesitylene and in particular toluene.

Examples of suitable polar-aprotic solvents are N,N-disubstituted aliphatic carboxamides (especially N,N-di-$C_1$-$C_4$-alkyl-$C_1$-$C_4$-carboxamides), nitrogen-containing heterocycles and aprotic ethers (especially cyclic ethers, diaryl ethers and di-$C_1$-$C_6$-alkyl ethers of monomeric and oligomeric $C_2$-$C_3$-alkylene glycols which may comprise up to 6 alkylene oxide units, in particular diethylene glycol di-$C_1$-$C_4$-alkyl ethers).

Examples of particularly suitable solvents include: N,N-dimethylformamide, N,N-diethylformamide, N,N-dimethylacetamide and N,N-dimethylbutyramide; N-methyl-2-pyrrolidone, quinoline, isoquinoline, quinaldine, pyrimidine, N-methylpiperidine and pyridine; tetrahydrofuran, dioxane, diphenyl ether, the dimethyl, diethyl, dipropyl, diisopropyl, di-n-butyl, di-sec-butyl and di-tert-butyl ethers of diethylene glycol, diethylene glycol methyl ethyl ether, triethylene glycol dimethyl ether, triethylene glycol diethyl ether and triethylene glycol methyl ethyl ether.

The amount of solvent is generally from 10 to 1000 ml, preferably from 20 to 300 ml, per g of halogenated aromatic.

Suitable transition metal catalysts are in particular palladium complexes, which are in turn generally used in amounts of from 1 to 20 mol %, in particular from 2 to 10 mol %, based on the halogenated aromatic. The additional presence of free ligand molecules is typically not required.

Examples of such catalysts are tetrakis(triphenylphosphine)palladium(0), tetrakis(tris-o-tolylphosphine)palladium (0), [1,2-bis(diphenylphosphino)ethane]palladium(11) chloride, [1,1'-bis(diphenylphosphino)ferrocene]palladium (II) chloride, bis(triethylphosphine)-palladium(II) chloride, bis(tricyclohexylphosphine)palladium(II) acetate, (2,2'-bipyridyl)palladium(II) chloride, bis(triphenylphosphine)palladium(II) chloride, tris(dibenzylideneacetone)dipalladium (0), 1,5-cyclooctadienepalladium(II) chloride, bis (acetonitrile)palladium(II) chloride and bis(benzonitrile) palladium(II) chloride, palladium(II) acetate, preference being given to [1,1'-bis(diphenylphosphino)ferrocene]palladium(II) chloride, tetrakis(triphenylphosphine)palladium(0) and palladium(II) acetate.

In general, the simultaneous presence of free ligand molecules is advisable, for example of tri(tert-butyl)phosphine, tri(i-butyl)phosphine, triphenylphosphine and tris(o-tolyl) phosphine, and 2-dicyclohexylphosphino-2,6-dimethoxybiphenyl. Typical amounts are from 80 to 500 mol %, preferably from 100 to 300 mol %, based on the transition metal catalyst.

Useful bases preferably include the alkali metal salts, especially the sodium salts and in particular the potassium salts, weak organic and inorganic acids, such as sodium acetate, potassium acetate, sodium carbonate, sodium hydrogencarbonate, potassium carbonate and potassium hydrogencarbonate, phosphate, fluorides such as potassium fluoride. Preferred bases are the acetates, in particular potassium acetate.

In general, from 1 to 5 mol, preferably from 2 to 4 mol, of base are used per mole of halogenated aromatic.

The reaction temperature is typically from 20 to 180° C., in particular from 60 to 120° C.

The reaction time is generally from 0.5 to 30 h, in particular from 1 to 20 h.

In terms of process technology, the procedure in the preparation of the boronic acid derivatives is appropriately as follows:

The halogenated aromatic and solvent are initially charged, the diborane of the general formula (IV), the transition metal catalyst and the base are added successively and the mixture is heated to the desired reaction temperature under protective gas for from 0.5 to 30 h. After cooling to room temperature, the solid constituents are filtered out of the reaction mixture and the solvent is distilled off under reduced pressure.

The Suzuki reaction of the boronic acid derivative thus prepared with the corresponding halogenated aromatic can in principle be used to prepare the product in step (a) of the process according to the invention under analogous conditions, in which case the corresponding boronic acid derivative instead of the diborane is reacted with the appropriate halogenated aromatic.

However, preference is given to reacting the boronic acid derivative with the halogenated aromatic in the presence of an organic solvent, if desired in a mixture with water, and of a transition metal catalyst and of a base, the molar ratio of boronic acid derivative to halogenated aromatic being generally from 0.8:1 to 3:1, preferably from 0.9:1 to 2:1.

Suitable solvents are all solvents in which the reactants dissolve completely at reaction temperature and the catalysts and bases used at least partially, so that substantially homogeneous reaction conditions are present.

Suitable examples are octane, isooctane, nonane, isononane, decane, isodecane, undecane, dodecane, hexadecane and octadecane, cycloheptane, cyclooctane, methylcyclohexane, dimethylcyclohexane, trimethylcyclohexane, ethylcyclohexane, diethylcyclohexane, propylcyclohexane, isopropylcyclohexane, dipropylcyclohexane, butylcyclohexane, tert-butylcyclohexane, methylcycloheptane and methylcyclooctane, toluene, o-, m- and p-xylene, 1,3,5-trimethylbenzene (mesitylene), 1,2,4- and 1,2,3-trimethylbenzene, ethylbenzene, propylbenzene, isopropylbenzene, butylbenzene, isobutylbenzene, tert-butylbenzene and cyclohexylbenzene; naphthalene, decahydronaphthalene (decalin), 1- and 2-methylnaphthalene and 1- and 2-ethylnaphthalene; combinations of the aforementioned solvents, as can be obtained from the high-boiling, partly or fully hydrogenated fractions of thermal and catalytic cracking processes in crude oil or naphtha processing, for example mixtures of the Exsol® type and alkylbenzene mixtures of the Solvesso® type.

Very particularly preferred solvents are xylene (all isomers), mesitylene and in particular toluene.

The amount of solvent is typically from 10 to 1000 ml, preferably from 20 to 100 ml, per g of boronic acid derivative.

Preference is given to using water as an additional solvent. In this case, generally from 10 to 1000 ml, in particular from 250 to 500 ml, of water are used per l of organic solvent.

The transition metal catalysts used are likewise preferably palladium complexes. The amount of catalyst used is typically from 1 to 20 mol %, in particular from 1.5 to 5 mol %, based on the boronic acid derivative.

In general, the simultaneous presence of free ligand molecules is advisable, for example of tri(tert-butyl)phosphine, tri(i-butyl)phosphine, triphenylphosphine and tris(o-tolyl) phosphine and 2-dicyclohexylphosphino-2,6-dimethoxybiphenyl. Typical amounts are from 80 to 500 mol %, preferably from 100 to 300 mol %, based on the transition metal catalyst.

Preferred bases are alkali metal salts of weak acids, particular preference being given to the carbonates, such as sodium carbonate and in particular potassium carbonate. Preference is also given here to phosphates, such as sodium phosphate or potassium phosphate. In general, the amount of bases is from 0.1 to 10 mol, in particular from 0.2 to 5 mol, per mole of boronic acid derivative.

The reaction temperature is generally from 20 to 180° C., preferably from 60 to 120° C. When water is used, it is advisable not to undertake the reaction at temperatures above 100° C., since it is otherwise necessary to work under pressure.

The reaction has typically ended within from 0.5 to 48 h, in particular within from 5 to 20 h.

In terms of process technology, the procedure is appropriately as follows:

The boronic acid derivative and the halogenated aromatic and solvent are initially charged, transition metal catalyst and the base, preferably dissolved in water or a water/alcohol mixture, are added, and the mixture is heated to the desired reaction temperature under protective gas or from 0.5 to 48 h. After cooling to room temperature, the organic phase is separated from the reaction mixture and the solvent is distilled off under reduced pressure.

The purity of the thus prepared product from step (a) of the process according to the invention for preparing the heptarylene- and octarylenetetracarboximides is generally sufficient for the further reaction in step (b). If appropriate, the crude product can be purified further by washing with water and, if desired, a suitable organic solvent, especially a chlorinated aliphatic or aromatic hydrocarbon, or by column chromatography on silica gel with a mixture of methylene chloride and hexane or pentane or with toluene as the eluent.

The yield in step a) of the process according to the invention is typically from 50 to 90%.

In addition to the above-described Suzuki reaction, which requires a corresponding boronic acid derivative, a direct coupling, especially in the case of homo couplings, of halides can also be effected.

In this case, the reaction of the correspondingly halogenated aromatics of the formula (II) and (III) can be effected in the presence of a diborane of the general formula (IV). Finally, a Suzuki reaction likewise proceeds, except that the corresponding boronic acid derivative is generated only in situ.

The coupling can be effected, for example, in the presence of from 30 to 70 mol %, based on the halogenated aromatic, of a diborane of the general formula (IV), of a transition metal catalyst, of a base and of an aprotic solvent by a Suzuki coupling reaction, in which case the boronic acid derivative formed in situ is not intermediately isolated but rather reacted directly with the remaining halogenated aromatic.

In this process variant, the procedure is analogous to the above, except that, for example, only from 30 to 70 mol % of diborane of the general formula (IV), based on the halogenated aromatic, is used.

In general, from 1 to 20 mol %, preferably from 5 to 10 mol %, of transition metal catalyst, and from 1 to 5 mol, preferably from 2 to 3 mol, of base are used per mole of halogenated aromatic. The aprotic organic solvent is used typically in amounts of from 10 to 100 ml, in particular from 20 to 50 ml, per g of halogenated aromatic.

The reaction temperature is generally from 20 to 100° C., preferably from 60 to 80° C., and the reaction time is from 12 to 72 h, preferably from 24 to 48 h.

In terms of process technology, the procedure is appropriately as follows:

The halogenated aromatic and solvent are initially charged, the diborane of the general formula (IV), the transition metal catalyst and the base are added in succession, and the mixture is heated to the desired reaction temperature for from 12 to 72 h. After cooling to room temperature, the organic phase is removed from the reaction mixture and the solvent is distilled off under reduced pressure.

Here too, the purity of the resulting product is generally sufficient for the subsequent cyclodehydrogenation in step (b) of the process according to the invention. Further purification is possible, for example, by column chromatography.

The yield is typically from 80 to 95%.

An additional possibility is to perform a direct coupling of the halogenated aromatics without using a diborane.

This coupling can be effected, for example, in the presence of an organic transition metal complex as a catalyst, free ligand molecules and an aprotic solvent in a homo coupling.

Suitable inert diluents are, for example, aliphatic carboxamides such as N,N-dimethylformamide and N,N-dimethylacetamide, aliphatic and cycloaliphatic ethers such as 1,2-dimethoxyethane, and aromatics such as benzene, toluene and xylene, preference being given to N,N-dimethylformamide and N,N-dimethylacetamide.

The amount of diluent is generally from 20 to 100 g, preferably from 25 to 45 g, per gram of halogen compound.

Useful organic transition metal complexes which serve as the catalyst include, as well as the known palladium complexes such as tetrakis(triphenylphospine)palladium(0), especially nickel complexes, for example bis(triphenylphosphine)nickel(II) chloride, tetrakis(triphenylphosphine)nickel (0), [1,2-bis(diphenylphosphino)ethane]nickel(II) chloride and preferably bis(1,5-cyclooctadiene)nickel(0). The catalysts can also be obtained by the addition of transition metal salts or compounds, free ligands such as cyclooctadiene, bipyridyl, triphenylphosphine, trifluorophosphine, $\eta$-, $\delta$- and $\pi$-bonded olefines, cycloolefines, aromatics and antiaromatics, carbonyls, hydrogen and halogen, and also mixtures thereof, and, if required, oxidation and reducing agents.

In general, from 40 to 150 mol %, preferably from 50 to 100 mol %, of organic transition metal complex based on the halogen compound used are used.

In general, the simultaneous presence of free ligand molecules is always advisable, especially mixtures of cyclooctadiene and bipyridyl in a molar ratio of from 1:1 to 8:1. Suitable amounts here are typically from 80 to 900 mol %, preferably from 80 to 200 mol %, preferably based on the halogen compound.

The coupling temperature is generally from 40 to 80° C., preferably from 60 to 70° C.

The reaction time is generally from 24 to 48 h, in particular from 36 to 48 h.

In terms of process technology, the procedure in this direct coupling is appropriately to initially charge the halogen compound, the organometallic catalyst and free ligand molecules in the inert diluent and, if appropriate under protective gas, to heat to the desired reaction temperature for from 24 to 48 h. After cooling, the reaction mixture is introduced into water which may comprise methanol if appropriate, dilute inorganic acid, for example dilute hydrochloric acid, is added in and the precipitate formed is filtered off, washed with water and dried under reduced pressure.

The purity of the inventive product thus produced is generally sufficient for the subsequent cyclodehydrogenation in step (b) of the process according to the invention. If appropriate, the product may additionally be purified further by column chromatography on silica gel with a mixture of methylene chloride and hexane or pentane as the eluent.

The yield is generally from 70 to 90%.

In step (b) of the process according to the invention, the cyclodehydrogenation of the reaction product obtained in step (a) takes place. The cyclodehydrogenation can be undertaken in an organic reaction medium which has hydroxyl and amino functions and comprises an essentially undissolved base or in the presence of a base-stable high-boiling organic solvent and of an alkali metal or alkaline earth metal base and a nitrogen-containing auxiliary base.

Preference is given to the former process variant. Suitable organic reaction media here are in particular amino alcohols which have from 2 to 20, preferably from 2 to 10 carbon atoms. The carbon chain of these alcohols can be interrupted by oxygen atoms in ether function. Examples of particularly suitable solvents are ethanolamine, triethanolamine and diethanolamine, preference being given to ethanolamine. It is also possible to use mixtures of alcohols and amines which each have a boiling point of at least 70° C. and are liquid at the reaction temperature.

Typically, from 1.5 to 150 ml, preferably from 5 to 50 ml, of reaction medium are used per gram of starting compound.

Suitable bases essentially insoluble in the reaction medium are the alkali metal salts, especially the sodium salts and in particular the potassium salts, weak organic and preferably weak inorganic acids, such as formates, acetates, propionates, hydrogencarbonates and more preferably carbonates, especially sodium carbonate and in particular potassium carbonate.

In general, the amount of base is from 1 to 10 mol, preferably from 2 to 5 mol, per mole of starting compound.

The reaction temperature is generally from 40 to 200° C., in particular from 80 to 160° C.

The reaction time is typically from 0.5 to 24 h, preferably from 1 to 12 h.

In terms of process technology, the procedure is appropriately to stir a mixture of starting compound, solvent and base at the desired reaction temperature under protective gas for from 0.5 to 24 h, and to precipitate the inventive product of the formula (I) formed, after cooling to room temperature, out of the reaction mixture by adding an alcohol, like ethanol, or water, to filter it off and to wash it with water.

The inventive diimides can be purified by removing catalyst residues by a rapid filtration through silica gel while washing it with a halogenated aliphatic hydrocarbon such as methylene chloride. Residues of unconverted reactants can be removed by column chromatography on silica gel with methylene chloride as the eluent or by repeated washing with hexane or pentane.

The yield is generally from 90 to 100%.

The product obtained by the process according to the invention for preparing heptarylene- and octarylenetetracarboximides is diimides of the general formula (I)

stituted by: $C_1$-$C_{12}$-alkoxy, $C_1$-$C_6$-alkylthio, —C≡$CR^1$, —$CR^1$=$CR^1{}_2$, hydroxyl, mercapto, halogen, cyano, nitro, —$NR^2R^3$, —$NR^2COR^3$, —$CONR^2R^3$, —$SO_2NR^2R^3$, —$COOR^2$, —$SO_3R^2$, —$PR^2R^3$, —$POR^2R^3$, aryl and/or saturated or unsaturated $C_4$-$C_7$-cycloalkyl whose carbon skeleton may be interrupted by one or more —O—, —S—, —$NR^1$—, —N=$CR^1$—, —$CR^1$=$CR^1$—, —CO—, —SO— and/or —$SO_2$— moieties, where the aryl and cycloalkyl radicals may each be mono- or poly-substituted by $C_1$-$C_{18}$-alkyl and/or the above radicals specified as substituents for alkyl;

(ii) $C_3$-$C_8$-cycloalkyl whose carbon skeleton may be interrupted by one or more —O—, —S—, —$NR^1$—, —N=$CR^1$—, —$CR^1$=$CR^1$—, —CO—, —SO— and/or —$SO_2$— moieties and to which may be fused further saturated or unsaturated 5- to 7-membered rings whose carbon skeleton may be interrupted by one or more —O—, —S—, —$NR^1$—, —N=$CR^1$—, —$CR^1$=$CR^1$—, —CO—, —SO— and/or —$SO_2$— moieties, where the entire ring system may be mono- or polysubstituted by: $C_1$-$C_{18}$-alkyl, $C_1$-$C_{12}$-alkoxy, $C_1$-$C_6$-alkylthio, —C≡$CR^1$, —$CR^1$=$CR^1{}_2$, hydroxyl, mercapto, halogen, cyano, nitro, —$NR^2R^3$, —$NR^2COR^3$, —$CONR^2R^3$, —$SO_2NR^2R^3$, —$COOR^2$, —$SO_3R^2$, —$PR^2R^3$ and/or —$POR^2R^3$;

(iii) aryl or hetaryl to which may be fused further saturated or unsaturated 5- to 7-membered rings whose carbon skeleton may be interrupted by one or more —O—, —S—, —$NR^1$—, —N=$CR^1$—, —$CR^1$=$CR^1$—, —CO—, —SO— and/or —$SO_2$— moieties, where the entire ring system may be mono- or polysubstituted by: $C_1$-$C_{18}$-alkyl, $C_1$-$C_{12}$-alkoxy, $C_1$-$C_6$-alkylthio, —C≡$CR^1$, —$CR^1$=$CR^1{}_2$, hydroxyl, mercapto, halogen, cyano, nitro, —$NR^2R^3$, —$NR^2COR^3$, —$CONR^2R^3$, —$SO_2NR^2R^3$, —$COOR^2$, —$SO_3R^2$, —$PR^2R^3$, —$POR^2R^3$, aryl and/or hetaryl, each of which may be substituted by $C_1$-$C_{18}$-alkyl, $C_1$-$C_{12}$-alkoxy,

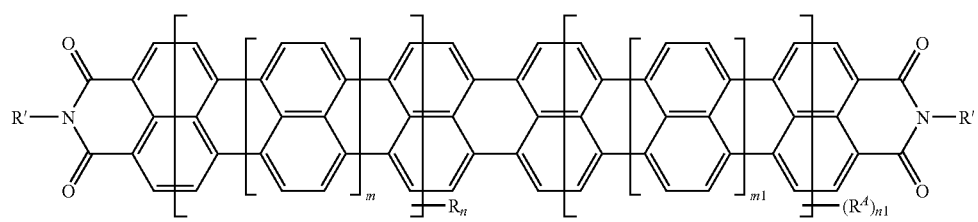

(I)

or mixtures thereof.

In this structure, the variables R, $R^A$, R' are each defined as follows:

Each R, $R^A$ are independently identical or different radicals selected from the following:

aryloxy, arylthio, hetaryloxy or hetarylthio, to each of which may be fused further saturated or unsaturated 5- to 7-membered rings whose carbon skeleton may be interrupted by one or more —O—, —S—, —$NR^1$—, —N=$CR^1$—, —CO—, —SO— and/or —$SO_2$— moieties, where the entire ring system may be mono- or polysubstituted by the (i), (ii), (iii), (iv) and/or (v) radicals:

(i) $C_1$-$C_{30}$-alkyl whose carbon chain may be interrupted by one or more —O—, —S—, —$NR^1$—, —N=$CR^1$—, —C≡C—, —$CR^1$=$CR^1$—, —CO—, —SO— and/or —$SO_2$— moieties and which may be mono- or polysubhydroxyl, mercapto, halogen, cyano, nitro, —$NR^2R^3$, —$NR^2COR^3$, —$CONR^2R^3$, —$SO_2NR^2R^3$, —$COOR^2$, —$SO_3R^2$, —$PR^2R^3$ and/or —$POR^2R^3$;

(iv) a —U-aryl radical which may be mono- or polysubstituted by the above radicals specified as substituents for the aryl radicals (iii), where U is a —O—, —S—, —$NR^1$—, —CO—, —SO— or —$SO_2$— moiety;

(v) $C_1$-$C_{12}$-alkoxy, $C_1$-$C_6$-alkylthio, —C≡$CR^1$, —$CR^1$=$CR^1{}_2$, hydroxyl, mercapto, halogen, cyano, nitro, —$NR^2R^3$, —$NR^2COR^3$, —$CONR^2R^3$, —$SO_2NR^2R^3$, —$COOR^2$, —$SO_3R^2$, —$PR^2R^3$ and/or —$POR^2R^3$;

each R' is independently hydrogen;

$C_1$-$C_{30}$-alkyl whose carbon chain may be interrupted by one or more —O—, —S—, —$NR^1$—, —N=$CR^1$—, —C≡C—, —$CR^1$=$CR^1$—, —CO—, —SO— and/or —SO$_2$— moieties and which may be mono- or polysubstituted by the (ii), (iii), (iv) and/or (v) radicals specified as substituents for the R radicals;

C$_3$-C$_8$-cycloalkyl to which may be fused further saturated or unsaturated 5- to 7-membered rings whose carbon skeleton may be interrupted by one or more —O—, —S—, —NR$^1$—, —N=CR$^1$—, —CR$^1$=CR$^1$—, —CO—, —SO— and/or —SO$_2$— moieties, where the entire ring system may be substituted by the (i), (ii), (iii), (iv) and/or (v) radicals specified as substituents for the R radicals; or aryl or hetaryl to which may be fused further saturated or unsaturated 5- to 7-membered rings whose carbon skeleton may be interrupted by one or more —O—, —S—, —NR$^1$—, —N=CR$^1$—, —CR$^1$=CR$^1$—, —CO—, —SO— and/or —SO$_2$— moieties, where the entire ring system may be substituted by the (i), (ii), (iii), (iv), (v) radicals specified as substituents for the R radicals, aryl- and/or hetarylazo, each of which may be substituted by C$_1$-C$_{10}$-alkyl, C$_1$-C$_6$-alkoxy and/or cyano;

In this structure, the variables R", R$^1$ to R$^2$ are each defined as follows: each R" is independently hydrogen, C$_1$-C$_{30}$-alkyl, C$_5$-C$_8$-cycloalkyl, aryl or hetaryl or joined together with formation of a 5- to -7-membered ring which comprises the two oxygen atoms and also the boron atom, to which may be fused unsaturated or saturated rings and which may be substituted on the carbon atoms by up to 4 C$_1$-C$_{30}$-alkyl, C$_5$-C$_8$-cycloalkyl, aryl or hetaryl groups;

R$^1$ is hydrogen or C$_1$-C$_{18}$-alkyl, where the R$^1$ radicals may be the same or different when they occur more than once;

R$^2$, R$^3$ are each independently hydrogen;

C$_1$-C$_{18}$-alkyl whose carbon chain may be interrupted by one or more —O—, —S—, —CO—, —SO— and/or —SO$_2$— moieties and which may be mono- or polysubstituted by C$_1$-C$_{12}$-alkoxy, C$_1$-C$_6$-alkylthio, hydroxyl, mercapto, halogen, cyano, nitro and/or —COOR$^1$;

aryl or hetaryl to each of which may be fused further saturated or unsaturated 5- to 7-membered rings whose carbon skeleton may be interrupted by one or more —O—, —S—, —CO— and/or —SO$_2$— moieties, where the entire ring system may be mono- or polysubstituted by C$_1$-C$_{12}$-alkyl and/or the above radicals specified as substituents for alkyl.

Specific examples of the R, R$^4$, R', R", R$^1$ to R$^3$ radicals mentioned in the formulae and their substituents include:

Examples of alkyls are methyl, ethyl, propyl, isopropyl, butyl, isobutyl, tert-butyl, pentyl, isopentyl, neopentyl, tert-pentyl, hexyl, 2-methylpentyl, heptyl, 1-ethylpentyl, octyl, 2-ethylhexyl, isooctyl, nonyl, isononyl, decyl, isodecyl, undecyl, dodecyl, tridecyl, isotridecyl, tetradecyl, pentadecyl, hexadecyl, heptadecyl, octadecyl, nonadecyl and eicosyl (the above terms isooctyl, isononyl, isodecyl and isotridecyl are trivial terms and stem from the alcohols obtained by the oxo process). The numbers specified as indices after the symbol "C" refer to the maximum and minimum number of carbon atoms in the alkyls.

Examples of alkyls interrupted by oxygen are 2-methoxyethyl, 2-ethoxyethyl, 2-propoxyethyl, 2-isopropoxyethyl, 2-butoxyethyl, 2- and 3-methoxypropyl, 2- and 3-ethoxypropyl, 2- and 3-propoxypropyl, 2- and 3-butoxypropyl, 2- and 4-methoxybutyl, 2- and 4-ethoxybutyl, 2- and 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- and 4-butoxybutyl, 4,8-dioxadecyl, 3,6,9-trioxadecyl, 3,6,9-trioxaundecyl, 3,6,9-trioxadodecyl, 3,6,9,12-tetraoxatridecyl and 3,6,9,12-tetraoxatetradecyl.

Examples of alkyls interrupted by sulfur are 2-methylthioethyl, 2-ethylthioethyl, 2-propylthioethyl, 2-isopropylthioethyl, 2-butylthioethyl, 2- and 3-methylthiopropyl, 2- and 3-ethylthiopropyl, 2- and 3-propylthiopropyl, 2- and 3-butylthiopropyl, 2- and 4-methylthiobutyl, 2- and 4-ethylthiobutyl, 2- and 4-propylthiobutyl, 3,6-dithiaheptyl, 3,6-dithiaoctyl, 4,8-dithianonyl, 3,7-dithiaoctyl, 3,7-dithianonyl, 2- and 4-butylthiobutyl, 4,8-dithiadecyl, 3,6,9-trithiadecyl, 3,6,9-trithiaundecyl, 3,6,9-trithiadodecyl, 3,6,9,12-tetrathiatridecyl and 3,6,9,12-tetrathiatetradecyl.

Examples of alkyls interrupted by amino groups are 2-monomethyl- and 2-monoethylam inoethyl, 2-dimethylaminoethyl, 2- and 3-dimethylaminopropyl, 3-monoisopropylaminopropyl, 2- and 4-monopropylaminobutyl, 2- and 4-dimethylaminobutyl, 6-methyl-3,6-diazaheptyl, 3,6-dimethyl-3,6-diazaheptyl, 3,6-diazaoctyl, 3,6-dimethyl-3,6-diazaoctyl, 9-methyl-3,6,9-triazadecyl, 3,6,9-trimethyl-3,6,9-triazadecyl, 3,6,9-triazaundecyl, 3,6,9-trimethyl-3,6,9-triazaundecyl, 12-methyl-3,6,9,12-tetraazatridecyl and 3,6,9,12-tetramethyl-3,6,9,12-tetraazatridecyl.

Further examples of alkyl groups which are interrupted and/or have substituents are:

(1-ethylethylidene)aminoethylene, (1-ethylethylidene)aminopropylene, (1-ethylethylidene)aminobutylene, (1-ethylethylidene)aminodecylene and (1-ethylethylidene)aminododecylene;

propan-2-on-1-yl, butan-3-on-1-yl, butan-3-on-2-yl and 2-ethylpentan-3-on-1-yl;

2-methylsulfoxidoethyl, 2-ethylsulfoxidoethyl, 2-propylsulfoxidoethyl, 2-isopropylsulfoxidoethyl, 2-butylsulfoxidoethyl, 2- and 3-methylsulfoxidopropyl, 2- and 3-ethylsulfoxidopropyl, 2- and 3-propylsulfoxidopropyl, 2- and 3-butylsulfoxidopropyl, 2- and 4-methylsulfoxidobutyl, 2- and 4-ethylsulfoxidobutyl, 2- and 4-propylsulfoxidobutyl and 4-butylsulfoxidobutyl;

2-methylsulfonylethyl, 2-ethylsulfonylethyl, 2-propylsulfonylethyl, 2-isopropylsulfonylethyl, 2-butylsulfonylethyl, 2- and 3-methylsulfonylpropyl, 2- and 3-ethylsulfonylpropyl, 2- and 3-propylsulfonylpropyl, 2- and 3-butylsulfonylpropyl, 2- and 4-methylsulfonylbutyl, 2- and 4-ethylsulfonylbutyl, 2- and 4-propylsulfonylbutyl and 4-butylsulfonylbutyl;

carboxymethyl, 2-carboxyethyl, 3-carboxypropyl, 4-carboxybutyl, 5-carboxypentyl, 6-carboxyhexyl, 8-carboxyoctyl, 10-carboxydecyl, 12-carboxydodecyl and 14-carboxytetradecyl;

sulfomethyl, 2-sulfoethyl, 3-sulfopropyl, 4-sulfobutyl, 5-sulfopentyl, 6-sulfohexyl, 8-sulfooctyl, 10-sulfodecyl, 12-sulfododecyl and 14-sulfotetradecyl;

2-hydroxyethyl, 2- and 3-hydroxypropyl, 1-hydroxyprop-2-yl, 3- and 4-hydroxybutyl, 1-hydroxybut-2-y1 and 8-hydroxy-4-oxaoctyl;

2-cyanoethyl, 3-cyanopropyl, 3- and 4-cyanobutyl, 2-methyl-3-ethyl-3-cyanopropyl, 7-cyano-7-ethylheptyl and 4,7-dimethyl-7-cyanoheptyl;

2-chloroethyl, 2- and 3-chloropropyl, 2-, 3- and 4-chlorobutyl, 2-bromoethyl, 2- and 3-bromopropyl and 2-, 3- and 4-bromobutyl;

2-nitroethyl, 2- and 3-nitropropyl and 2-, 3- and 4-nitrobutyl.

Examples of alkyloxy are methoxy, ethoxy, propoxy, isopropoxy, butoxy, isobutoxy, secbutoxy, tert-butoxy, pentoxy, isopentoxy, neopentoxy, tert-pentoxy and hexoxy.

Examples of alkylthio are methylthio, ethylthio, propylthio, isopropylthio, butylthio, isobutylthio, sec-butylthio, tert-butylthio, pentylthio, isopentylthio, neopentylthio, tert-pentylthio and hexylthio.

Examples of radicals with a triple bond are ethynyl, 1- and 2-propynyl, 1-, 2- and 3-butynyl, 1-, 2-, 3- and 4-pentynyl, 1-, 2-, 3-, 4- and 5-hexynyl, 1-, 2-, 3-, 4-, 5-, 6-, 7-, 8-, and 9-decynyl, 1-, 2-, 3-, 4-, 5-, 6-, 7-, 8-, 9-, 10- and 11-dodecynyl and 1-, 2-, 3-, 4-, 5-, 6-, 7-, 8-, 9-, 10-, 11-, 12-, 13-, 14-, 15-, 16- and 17-octadecynyl.

Examples of radicals with a double bond are ethenyl, 1- and 2-propenyl, 1-, 2- and 3-butenyl, 1-, 2-, 3- and 4-pentenyl, 1-, 2-, 3-, 4- and 5-hexenyl, 1-, 2-, 4-, 5-, 6-, 7-, 8-, and 9-decenyl, 1-, 2-, 3-, 4-, 5-, 6-, 7-, 8-, 9-, 10- and 11-dodecenyl and 1-, 2-, 3-, 4-, 5-, 6-, 7-, 8-, 9-, 10-, 11-, 12-, 13-, 14-, 15-, 16- and 17-octadecenyl.

Examples of further radicals are
methylamino, ethylamino, propylamino, isopropylamino, butylamino, isobutylamino, pentylamino, hexylamino, dimethylamino, methylethylamino, diethylamino, dipropylamino, diisopropylamino, dibutylamino, diisobutylamino, dipentylamino, dihexylamino, dicyclopentylamino, dicyclohexylamino, dicycloheptylamino, diphenylamino and dibenzylamino;
formylamino, acetylamino, propionylamino and benzoylamino;
carbamoyl, methylaminocarbonyl, ethylaminocarbonyl, propylaminocarbonyl, butylaminocarbonyl, pentylaminocarbonyl, hexylaminocarbonyl, heptylaminocarbonyl, octylaminocarbonyl, nonylaminocarbonyl, decylaminocarbonyl and phenylaminocarbonyl;
aminosulfonyl, N,N-dimethylaminosulfonyl, N,N-diethylaminosulfonyl, N-methyl-N-ethylaminosulfonyl, N-methyl-N-dodecylaminosulfonyl, N-dodecylaminosulfonyl, (N,N-dimethylamino)ethylaminosulfonyl, N,N-(propoxyethyl)dodecylaminosulfonyl, N,N-diphenylaminosulfonyl, N,N-(4-tert-butylphenyl)octadecylaminosulfonyl and N,N-bis(4-chlorophenyl)aminosulfonyl;
methoxycarbonyl, ethoxycarbonyl, propoxycarbonyl, isopropoxycarbonyl, hexoxycarbonyl, dodecyloxycarbonyl, octadecyloxycarbonyl, phenoxycarbonyl, (4-tert-butylphenoxy)carbonyl and (4-chlorophenoxy)carbonyl;
methoxysulfonyl, ethoxysulfonyl, propoxysulfonyl, isopropoxysulfonyl, butoxysulfonyl, isobutoxysulfonyl, tert-butoxysulfonyl, hexoxysulfonyl, dodecyloxysulfonyl, octadecyloxysulfonyl, phenoxysulfonyl, 1- and 2-naphthyloxysulfonyl, (4-tert-butylphenoxy)sulfonyl and (4-chlorophenoxy)sulfonyl;
diphenylphosphino, di-(o-tolyl)phosphino and diphenylphosphinoxido.

Halogens are chlorine, bromine and iodine.

Aryl- or hetarylazo are, for example, phenylazo, 2-naphthylazo, 2-pyridylazo and 2-pyrimidylazo.

Optionally substituted cycloalkyls are, for example, cyclopropyl, cyclobutyl, cyclopentyl, 2- and 3-methylcyclopentyl, 2- and 3-ethylcyclopentyl, cyclohexyl, 2-, 3- and 4-methylcyclohexyl, 2-, 3- and 4-ethylcyclohexyl, 3- and 4-propylcyclohexyl, 3- and 4-isopropylcyclohexyl, 3- and 4-butylcyclohexyl, 3- and 4-sec-butylcyclohexyl, 3- and 4-tert-butylcyclohexyl, cycloheptyl, 2-, 3- and 4-methylcycloheptyl, 2-, 3- and 4-ethylcycloheptyl, 3- and 4-propylcycloheptyl, 3- and 4-isopropylcycloheptyl, 3- and 4-butylcycloheptyl, 3- and 4-sec-butylcycloheptyl, 3- and 4-tert-butylcycloheptyl, cyclooctyl, 2-, 3-, 4- and 5-methylcyclooctyl, 2-, 3-, 4- and 5-ethylcyclooctyl and 3-, 4- and 5-propylcyclooctyl; 3- and 4-hydroxycyclohexyl, 3- and 4-nitrocyclohexyl and 3- and 4-chlorocyclohexyl. The numbers specified as indices after the symbol "C" refer to the minimum and maximum number of carbon atoms in the alkyls.

Examples of optionally interrupted cycloalkyls are
1-, 2- and 3-cyclopentenyl, 1-, 2-, 3- and 4-cyclohexenyl, 1-, 2- and 3-cycloheptenyl and 1-, 2-, 3- and 4-cyclooctenyl; 2-dioxanyl, 1-morpholinyl, 1-thiomorpholinyl, 2- and 3-tetrahydrofuryl, 1-, 2- and 3-pyrrolidinyl, 1-piperazyl, 1-diketopiperazyl and 1-, 2-, 3- and 4-piperidyl.

Optionally fused and/or substituted and/or interrupted aryl and hetaryl groups should have at least from 3 to 14 ring atoms, preferably from 5 to 10 ring atoms, and are, for example,
phenyl, 2-naphthyl, 2- and 3-pyrryl, 2-, 3- and 4-pyridyl, 2-, 4- and 5-pyrimidyl, 3-, 4- and 5-pyrazolyl, 2-, 4- and 5-imidazolyl, 2-, 4- and 5-thiazolyl, 3-(1,2,4-triazyl), 2-(1,3,5-triazyl), 6-quinaldyl, 3-, 5-, 6- and 8-quinolinyl, 2-benzoxazolyl, 2-benzothiazolyl, 5-benzothiadiazolyl, 2- and 5-benzimidazolyl and 1- and 5-isoquinolyl;
1-, 2-, 3-, 4-, 5-, 6- and 7-indolyl, 1-, 2-, 3-, 4-, 5-, 6- and 7-isoindolyl, 5-(4-methylisoindolyl), 5-(4-phenylisoindolyl), 1-, 2-, 4-, 6-, 7- and 8-(1,2,3,4-tetrahydroisoquinolinyl), 3-(5-phenyl)-(1,2,3,4-tetrahydroisoquinolinyl), 5-(3-dodecyl-(1,2,3,4-tetrahydro-isoquinolinyl), 1-, 2-, 3-, 4-, 5-, 6-, 7- and 8-(1,2,3,4-tetrahydroquinolinyl) and 2-, 3-, 4-, 5-, 6-, 7-, and 8-chromanyl, 2-, 4- and 7-quinolinyl, 2-(4-phenylquinolinyl) and 2-(5-ethylquinolinyl);
2-, 3- and 4-methylphenyl, 2,4-, 3,5- and 2,6-dimethylphenyl, 2,4,6-trimethylphenyl, 2-, 3- and 4-ethylphenyl, 2,4-, 3,5- and 2,6-diethylphenyl, 2,4,6-triethylphenyl, 2-, 3- and 4-propylphenyl, 2,4-, 3,5- and 2,6-dipropylphenyl, 2,4,6-tripropylphenyl, 2-, 3- and 4-isopropylphenyl, 2,4-, 3,5- and 2,6-diisopropylphenyl, 2,4,6-triisopropylphenyl, 2-, 3- and 4-butylphenyl, 2,4-, 3,5- and 2,6-dibutylphenyl, 2,4,6-tributylphenyl, 2-, 3- and 4-isobutylphenyl, 2,4-, 3,5- and 2,6-diisobutylphenyl, 2,4,6-triisobutylphenyl, 2-, 3- and 4-sec-butylphenyl, 2,4-, 3,5- and 2,6-di-sec-butylphenyl and 2,4,6-tri-sec-butylphenyl; 2-, 3- and 4-methoxyphenyl, 2,4-, 3,5- and 2,6-dimethoxyphenyl, 2,4,6-trimethoxyphenyl, 2-, 3- and 4-ethoxyphenyl, 2,4-, 3,5- and 2,6-diethoxyphenyl, 2,4,6-triethoxyphenyl, 2-, 3- and 4-propoxyphenyl, 2,4-, 3,5- and 2,6-dipropoxyphenyl, 2-, 3- and 4-isopropoxyphenyl, 2,4- and 2,6-diisopropoxyphenyl and 2-, 3- and 4-butoxyphenyl;
2-, 3- and 4-chlorophenyl and 2,4-, 3,5- and 2,6-dichlorophenyl; 2-, 3- and 4-hydroxyphenyl and 2,4-, 3,5- and 2,6-dihydroxyphenyl; 2-, 3- and 4-cyanophenyl; 3- and 4-carboxyphenyl; 3- and 4-carboxamidophenyl, 3- and 4-N-methylcarboxamidophenyl and 3- and 4-N-ethylcarboxamidophenyl; 3- and 4-acetylaminophenyl, 3- and 4-propionylaminophenyl and 3- and 4-butyrylaminophenyl; 3- and 4-N-phenylaminophenyl, 3- and 4-N-(o-tolyl)aminophenyl, 3- and 4-N-(m-tolyl)aminophenyl and 3- and 4-N-(p-tolyl)aminophenyl; 3- and 4-(2-pyridyl)aminophenyl, 3- and 4-(3-pyridyl)aminophenyl, 3- and 4-(4-pyridyl)aminophenyl, 3- and 4-(2-pyrimidyl)aminophenyl and 4-(4-pyrimidyl)aminophenyl;
4-phenylazophenyl, 4-(1-naphthylazo)phenyl, 4-(2-naphthylazo)phenyl, 4-(4-naphthylazo)phenyl, 4-(2-pyridylazo)phenyl, 4-(3-pyridylazo)phenyl, 4-(4-pyridylazo)phenyl, 4-(2-pyrimidylazo)phenyl, 4-(4-pyrimidylazo)phenyl and 4-(5-pyrimidylazo)phenyl;
phenoxy, phenylthio, 2-naphthoxy, 2-naphthylthio, 2-, 3- and 4-pyridyloxy, 2-, 3- and 4-pyridylthio, 2-, 4- and 5-pyrimidyloxy and 2-, 4- and 5-pyrimidylthio.

The inventive diimides of the general formula (I) or mixtures thereof are preferably those in which R and $R^4$ are the same.

The inventive diimides of the general formula (I) or mixtures thereof are likewise preferably those in which R, $R^4$ are each independently aryloxy or arylthio, where the entire ring system may be mono- or polysubstituted by the (i), (ii), (iii), (iv) and/or (v) radicals as specified above. It is especially preferred when R, $R^A$ may each independently be mono- or polysubstituted by a (i) radical.

The inventive diimides of the general formula (I) or mixtures thereof are likewise preferably those in which R, $R^A$ are each independently

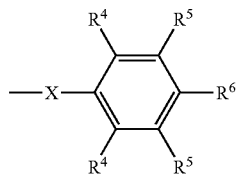

where
X is O or S and
$R^4, R^5, R^6$ may each independently be hydrogen or the (i), (ii), (iii), (iv) and/or (v) radicals as specified above, with the proviso that at least one of the $R^4, R^6$ radicals is not hydrogen. It is especially preferred that when $R^4$ is $C_1$-$C_{30}$-alkyl or $C_3$-$C_8$-cycloalkyl, a ternary carbon atom does not occur in the 1-position.

It is also preferred that neither $R^4$ is hydrogen and $R^5$, $R^6$ are each hydrogen, or $R^6$ is not hydrogen and $R^4$, $R^5$ are each hydrogen.

The inventive diimides of the general formula (I) or mixtures thereof are likewise preferably those in which each R' is independently $C_1$-$C_{30}$-alkyl or aryl, where the entire ring system may be mono- or polysubstituted by the (i), (ii), (iii), (iv) and/or (v) radicals as specified above. Especially preferably, R' is mono- or polysubstituted by a (i) radical. Likewise preferably, all R' are identical.

The inventive diimides of the general formula (I) exhibit strong absorption in the infrared region at wavelengths of from 750 to 1300 nm. Their functionalization can be selected in a controlled manner, such that they can be adjusted directly to the desired end use.

They are suitable for a multitude of uses, such as coloring high molecular weight organic and inorganic materials, for example of coatings, printing inks and plastics, for preparing aqueous polymer dispersions which absorb in the near infrared region of the electromagnetic spectrum, for obtaining markings and inscriptions which absorb infrared light and are invisible to the human eye, as infrared absorbers for heat management, as IR laser beam-absorbing materials in the fusion treatment of plastics parts, as semiconductors in organic electronics, as emitters in electro- and chemiluminescence applications, or as active components in photovoltaics.

The present invention further provides a process for preparing a quaterrylene compound of the general formula (II)

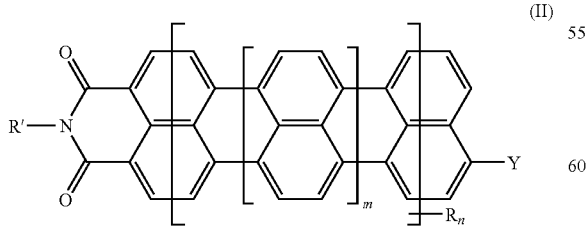

where Y is halogen and R', R, n, m are each as defined above, comprising the steps of (a) coupling at least one perylene compound of the formula (II)

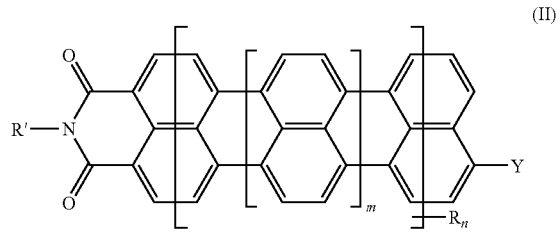

with at least one compound of the formula (IIIa) and/or (IIIa')

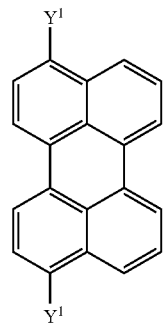

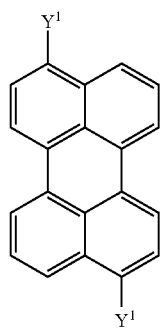

where
one radical of Y, $Y^1$ is halogen and the other is $B(OR'')_2$, m=0, and R, R', n are each as defined above to give a compound of the general formula (IIIb)/(IIIb')

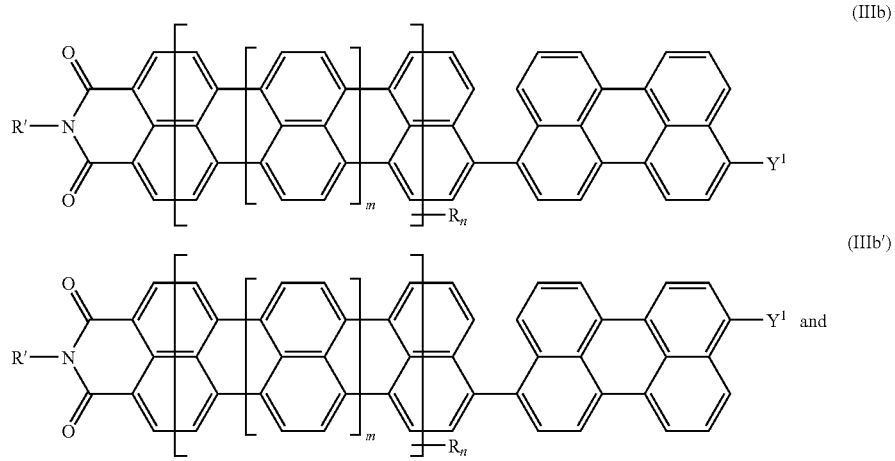

(IIIb)

(IIIb') and (b) cyclodehydrogenating the compound of the general formula (IIIb)/(IIIb') obtained in step (a) to give a rylene compound of the general formula (II), where $Y^1$ in formula (IIIb)/(IIIb') is as defined for Y in formula (II).

Such rylene compounds of the formula (II) are suitable, as mentioned above, as starting compounds for preparing heptarylene- and octarylenetetracarboximides and can be obtained with the aid of compounds of the formula (IIIb)/(IIIb'), said compounds of the formula (IIIb)/(IIIb') having been unknown to date.

The present invention therefore further provides a compound of the general formula (IIIb) or (IIIb')

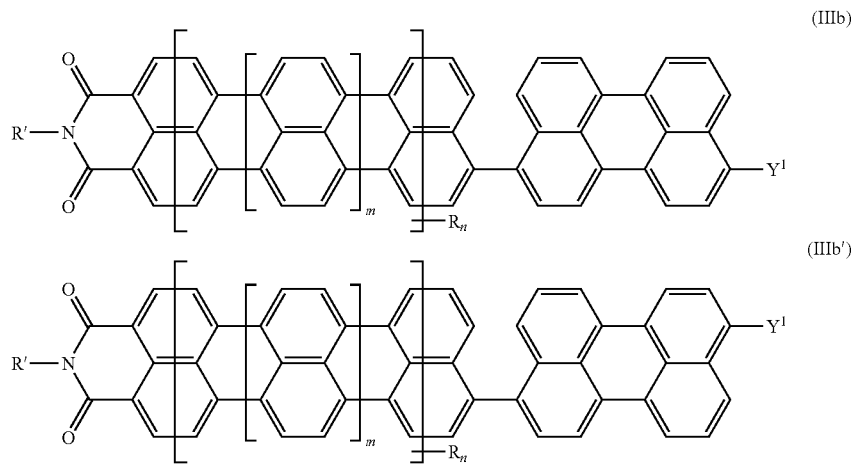

(IIIb)

(IIIb')

or mixtures thereof, where $Y^1$ is halogen or $B(OR'')_2$, m=0 and R, R', n are each as defined above. It is preferred here that $Y^1$ is halogen, especially bromine, such that the compound of the formula (IIIa) is 3,9(10)-dibromoperylene.

As detailed above, the reactions of step (a) and (b) are a Suzuki reaction and a cyclodehydrogenation, so that the statements made above apply analogously in principle.

In step (a), preference is given to using the compound of the formula (IIIa) in excess. The excess is preferably at least sevenfold. In step (b), the reaction is effected preferably in the presence of a metal salt, for example iron(III) chloride.

EXAMPLES

Example 1

Preparation of N-(2,6-diisopropylphenyl-1,6-bis[4-(1,1,3,3-tetramethylbutyl)phenoxy]-9-(7-[1(9)-bromo]perylene)perylene-3,4-dicarboximide First a solution of 0.5 ml of potassium carbonate in water (2M) and then 0.03 g (0.03 mmol) of $Pd(PPh_3)_4$ were added to a mixture, stirred under argon, of 0.51 g (0.5 mmol) of N-(2,6-diisopropylphenyl-4-(4,4,5,5-tetramethyl-1,3,2-dioxaboran-2-yl)-perylene-3,4-dicarboximide and 1.43 g (3.5 mmol) of 3,9(10)-dibromoperylene in 40 ml of toluene and 2 ml of ethanol. The mixture was heated to 70° C. under argon and stirred at this temperature for 6 h. After cooling to room temperature, the organic phase was removed and the solvent was drawn off under reduced pressure. The crude product was subjected to column chromatography on silica gel with toluene as the eluent.

0.42 g of product were obtained in the form of a red solid, which corresponds to a yield of 69%.

Analytical Data:

Rf=0.72 (toluene);

MS (FD): m/z (rel. int.)=1220.6 (100%) [M+];

¹H NMR (250 MHz, CD$_2$Cl$_2$, 25° C.): δ=9.48 (d, 1H, PMI H-7), 9.35 (d, 1H, PMI H-12), 8.20-8.40 (m, 2H, Ar—H), 8.26 (s, 1H, PMI H-5), 8.24 (s, 1H, PMI H-2), 8.09 (t, 2H, Ar—H), 7.80 (d, 1H, Ar—H), 7.64 (dd, 3H, Ar—H), 7.51-7.54 (m, 2H, Ar—H), 7.44 (d, 4H, phenoxy m-H), 7.32 (d, 4H, phenoxy o-H), 7.06-7.35 (m, 6H, Ar—H), 2.74 (sep, 2H, CH i-propyl), 1.74 (s, 4H), 1.38 (s, 12H), 1.12 (d, 12H), 0.73 (s, 9H), 0.72 (s, 9H);

¹³C NMR (62.9 MHz, CD$_2$Cl$_2$, 25° C.): 163.66, 154.20, 153.74, 146.45, 131.24, 130.09, 129.24, 128.46, 128.41, 127.31, 127.08, 124.40, 118.79, 118.63, 57.41, 38.64, 32.60, 31.85, 31.67, 29.43, 24.09.

Example 2

Preparation of N-(2,6-diisopropylphenyl-1,6-bis[4-(1,1,3,3-tetramethylbutyl)phenoxy]-13-bromoquaterrylene-3,4-dicarboximide A solution of 0.41 g (2.56 mmol) of iron(III) chloride in 2 ml of anhydrous nitromethane was added dropwise under argon to a solution of 0.2 g (0.16 mmol) of product of example 1 in 10 ml of methylene chloride. After a reaction time of 24 h at room temperature, the solvent was drawn off, and the reaction mixture was admixed with aqueous hydrochloric acid, filtered and washed with methanol. The crude product was subjected to column chromatography on silica gel with dichloromethan as the eluent.

0.12 g of product were obtained in the form of a green solid, which corresponds to a yield of 60%.
Analytical Data:
Rf=0.58 (toluene);
MS (FD): m/z (rel. int.) 1218.8 (100%), M+, 609.9 (40%), M/2;
UV-Vis (CH$_2$Cl$_2$): λ$_{max}$ (ε): 732 (177100), 668 (78000), 359 (17200), 260 (122000)

Example 3

Preparation of N-(2,6-diisopropylphenyl-1,6,11,15-tetra[4-(1,1,3,3-tetramethylbutyl)-phenoxy]-13-(11-[N-(2,6-diisopropylphenyl)]-1,6-bis[2,6-diisopropylphenoxy]terrylene-3,4-dicarboximide)quaterrylene-3,4-dicarboximide First a solution of 0.038 g (0.28 mmol) of potassium carbonate in 4 ml of water and 0.4 ml of ethanol and then 0.001 g (0.004 mmol) of palladium(II) acetate and 0.008 g (0.003 mmol) of 2-dicyclohexylphosphino-2,6-dimethoxybiphenyl were added to a mixture, stirred under N$_2$, of 0.057 g (0.04 mmol) of N-(2,6-diisopropylphenyl-1,6,9,14-tetra[2,6-diisopropylphenoxy]-11-(4,4,5,5-tetramethyl-1,3,2-dioxaboran-2-ypterrylene-3,4-dicarboximide and 0.063 g (0.04 mmol) of N-(2,6-diisopropylphenyl-1,6,11,15-tetra[4-(1,1,3,3-tetramethylbutyl)phenoxy]-13-chloroquaterrylene-3,4-dicarboximide in 15 ml of toluene. The mixture was heated to 85° C. under N$_2$ and stirred at this temperature for 14 h. After cooling to room temperature, the organic phase was removed and the solvent was drawn off under reduced pressure. The crude product was subjected to column chromatography on silica gel with toluene as the eluent.

60 mg of product were obtained in the form of a black-green solid, which corresponds to a yield of 52%.
Analytical Data:
Rf=0.2 (toluene);
MS (Maldi): m/z (rel. int.)=2853.5 (100%) [M+].

Example 4

Preparation of N-(2,6-diisopropylphenyl-1,6-bis[4-(1,1,3,3-tetramethylbutyl)phenoxy]-13-(13-[N-(2,6-diisopropylphenyl)]-1,6-bis[4-(1,1,3,3-tetramethylbutyl)phenoxy]quaterrylene-3,4-dicarboximide) quaterrylene-3,4-dicarboximide A solution of 0.017 g (0.1 mmol) of N-(2,6-diisopropylphenyl-1,6-bis[4-(1,1,3,3-tetramethylbutyl)phenoxy]-13-bromoquaterrylene-3,4-dicarboximide in 10 ml of toluene was added in a glovebox to a stirred mixture of 40 mg of Ni(cod)$_2$ and 0.1 ml of cyclooctadiene and 24 mg of 2,2'-bispyridyl in 15 ml of anhydrous DMF. The mixture was heated to 70° C. in the glovebox and stirred at this temperature for 48 h. After cooling to room temperature, the organic phase was removed and the solvent was drawn off under reduced pressure. The crude product was subjected to column chromatography on silica gel with CH$_2$Cl$_2$ as the eluent.

130 mg of product were obtained in the form of a black-green solid, which corresponds to a yield of 83%.
Analytical Data:
Rf=0.68 (toluene);
MS (Maldi): m/z (rel. int.)=2286.5 (100%) [M+].
UV-Vis (toluene): λ$_{max}$ (ε): 753 (340000), 687 (181000), 359 (39000).

Example 5

Preparation of N-(2,6-diisopropylphenyl-1,6,11,15-tetra[4-(1,1,3,3-tetramethylbutyl)phenoxy]-13-(13-[N-(2,6-diisopropylphenyl)]-1,6,11,15-tetra[4-(1,1,3,3-tetramethylbutyl)phenoxy]quaterrylene-3,4-dicarboximide)quaterrylene-3,4-dicarboximide 0.74 g (0.47 mmol) of N-(2,6-diisopropylphenyl-1,6,11,15-tetra[4-(1,1,3,3-tetramethylbutyl)phenoxy]-13-chloroquaterrylene-3,4-dicarboximide was stirred at room temperature under N$_2$ in 10 ml of toluene and 1 ml of water. After 10 min, 0.14 g (0.56 mmol) of bis(pinacolato)diboron, 0.22 g (0.94 mmol) of potassium phosphate monohydrate, 0.007 g (0.017 mmol) of 2-dicyclohexylphosphino-2,6-dimethoxybiphenyl and 0.002 g (0.008 mmol) of palladium(II) acetate were added thereto. The mixture was heated to 100° C. and stirred at this temperature for 24 h. The cooled reaction mixture was admixed with 50 ml of toluene and extracted with 50 ml of HCl (1M). The organic phase was dried over MgSO$_4$ and concentrated by evaporation. The residue was subjected to column chromatography on silica gel with dichloromethane:n-hexane (7:3) as the eluent.

0.46 g of product were obtained in the form of a black-green solid, which corresponds to a yield of 64%.
Analytical Data:
UV-Vis (CH$_2$Cl$_2$): λ$_{max}$ (ε)=773 (200 000 NA$^{-1}$cm$^{-1}$);
MS (Maldi): m/z (rel. int.)=3089.4 (100%) [M$^-$].

Example 6

Cyclodehydrorgenation to give N,N'-bis(2,6-diisopropylphenyl)-1,6,9,30-tetra(2,6-diisopropylphenylphenoxy)-12,17,22,27-tetra[4-(1,1,3,3-tetramethylbutyl)phenoxy]heptarylene-3,4:19,20-tetracarboximide A mixture of 0.03 g (0.01 mmol) of product of example 3, 0.063 g (0.5 mmol) of potassium carbonate and 10 ml of ethanolamine was heated to 120° C. under a nitrogen atmosphere. After 6 h, a large amount of reactant was still observed by means of TLC. After 30 h, the reactant had reacted completely.

After cooling, the reaction product was precipitated in water, filtered off, and washed with hot water and finally with hexane until the effluent became colorless. The residue was subjected to an overnight Soxhlet extraction with hexane. The product was dried at 70° C. under reduced pressure.

18 mg of product were obtained in the form of a black solid, which corresponds to a yield of 63%.

Analytical Data:

UV-Vis (CHCl$_3$): $\lambda_{max}$=973, 862 nm;

MS (Maldi): m/z (rel. int.)=2615.5 (100%) [M+].

Example 7

Cyclodehydrogenation to give N,N'-bis(2,6-diisopropylphenyl)-1,6,11,14,19,24,29,32-octa[4-(1,1,3,3-tetramethylbutyl)phenoxy]octarylene-3,4:21,22-tetracarboximide A mixture of 0.4 g (0.13 mmol) of product of example 5, 0.54 g (1.4 mmol) of potassium carbonate, 10 ml of ethanolamine and 5 ml of diethylene glycol diethyl ether was heated to 120° C. under a nitrogen atmosphere. The reaction was observed by TLC and UV-Vis spectrum every hour. After 3 hours, the reactant had been converted completely. After cooling, the reaction product was precipiated in 1M HCl, filtered off and washed with hot water until the effluent became colorless. The product was dried at 70° C. under reduced pressure.

0.4 g of product were obtained in the form of a black solid, which corresponds to a yield of 99%. The solution in CH$_3$Cl of the solid is almost colorless.

Analytical Data:

UV-Vis (CH$_2$Cl$_2$): $\lambda_{max}$ ($\epsilon$)=1066 nm (2 620 000 M$^{-1}$cm$^{-1}$);

MS (Maldi): m/z (rel. int.)=3087.5 (100%) [M+].

The invention claimed is:

1. A process comprising:

(a) coupling at least one quaterrylene compound of the formula (II)

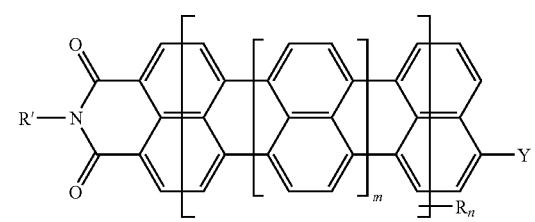

(II)

with at least one compound of the formula (III)

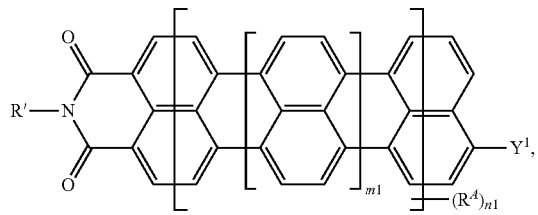

(III)

where

Y and Y$^1$ are each halogen, or one radical of Y and Y$^1$ is halogen and the other is B(OR")$_2$;

each R and R$^A$ are independently identical or different radicals selected from the following:

aryloxy, arylthio, hetaryloxy or hetarylthio, to each of which may be fused further saturated or unsaturated 5- to 7-membered rings whose carbon skeleton may be interrupted by one or more —O—, —S—, —NR$^1$—, —N=CR$^1$—, —CO—, —SO— and/or —SO$_2$— moieties, where the entire ring system may be mono- or polysubstituted by the (i), (ii), (iii), (iv) and/or (v) radicals:

(i) C$_1$-C$_{30}$-alkyl whose carbon chain may be interrupted by one or more —O—, —S—, NR$^1$, —N=CR$^1$—, —C≡C, —CR$^1$=CR$^1$—, —CO—, —SO— and/or —SO$_2$— moieties and which may be mono- or polysubstituted by: C$_1$-C$_{12}$-alkoxy, C$_1$-C$_6$-alkylthio, —C≡CR$^1$, —CR$^1$=CR$^1$$_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, —PR$^2$R$^3$, —POR$^2$R$^3$, aryl and/or saturated or unsaturated C$_4$-C$_7$-cycloalkyl whose carbon skeleton may be interrupted by one or more —O—, —S—, —NR$^1$, —N=CR$^1$—, —CR$^1$=CR$^1$—, —CO—, —SO— and/or —SO$_2$— moieties, where the aryl and cycloalkyl radicals may each be mono- or polysubstituted by C$_1$-C$_{18}$-alkyl and/or the above radicals specified as substituents for alkyl;

(ii) C$_3$-C$_8$-cycloalkyl whose carbon skeleton may be interrupted by one or more —O—, —S—, —NR$^1$, —N=CR$^1$—, —CR$^1$=CR$^1$—, —CO—, —SO— and/or —SO$_2$— moieties and to which may be fused further saturated or unsaturated 5- to 7-membered rings whose carbon skeleton may be interrupted by one or more —O—, —S—, —NR$^1$, —N=CR$^1$—, —CR$^1$=CR$^1$—, —CO—, —SO— and/or —SO$_2$-moieties, where the entire ring system may be mono- or polysubstituted by: C$_1$-C$_{18}$-alkyl, C$_1$-C$_{12}$-alkoxy, C$_1$-C$_6$-alkylthio, —C≡CR$^1$, —CR$^1$=CR$^1$$_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, —PR$^2$R$^3$ and/or —POR$^2$R$^3$;

(iii) aryl or hetaryl to which may be fused further saturated or unsaturated 5- to 7-membered rings whose carbon skeleton may be interrupted by one or more —O—, —S—, —N=CR$^1$—, —CR$^1$=CR$^1$—, —CO—, —SO— and/or —SO$_2$— moieties, where the entire ring system may be mono- or polysubstituted by: C$_1$-C$_{18}$-alkyl, C$_1$-C$_{12}$-alkoxy, C$_1$-C$_6$-alkylthio, —CR=CR$^1$, —CR$^1$=CR$^1$$_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, —PR$^2$R$^3$, —POR$^2$R$^3$, aryl and/or hetaryl, each of which may be substituted by C$_1$-C$_{18}$-alkyl, C$_1$-C$_{12}$-alkoxy, hydroxyl, mercapto, halogen, cyano, nitro, —NR²R³, —NR²COR³, CONR²R³, —SO₂NR²R³, —COOR², —SO₃R², —PR²R³ and/or —POR²R³;

(iv) a —U-aryl radical which may be mono- or polysubstituted by the above radicals specified as substituents for the aryl radicals (iii), where U is a —O—, —S—, NR¹, —CO—, —SO— or —SO₂— moiety;

(v) $C_1$-$C_{12}$-alkoxy, $C_1$-$C_6$-alkylthio, —C≡CR¹, —CR¹=CR¹₂, hydroxyl, mercapto, halogen, cyano, nitro, —NR²R³, —NR²COR³, —CONR²R³, —SO₂NR²R³, —COOR², —SO₃R², —PR²R³ and/or —POR²R³;

each R' is independently hydrogen;

$C_1$-$C_{30}$-alkyl whose carbon chain may be interrupted by one or more —O—, —S—, —NR¹, —N=CR¹—, —C≡C—, —CR¹=CR¹—, —CO—, —SO— and/or —SO₂— moieties and which may be mono- or polysubstituted by the (ii), (iii), (iv) and/or (v) radicals specified as substituents for the R radicals;

$C_3$-$C_8$-cycloalkyl to which may be fused further saturated or unsaturated 5- to 7-membered rings whose carbon skeleton may be interrupted by one or more —O—, —S—, —NR¹, —N=CR¹—, —CR¹=CR¹—, —CO—, —SO— and/or —SO₂— moieties, where the entire ring system may be substituted by the (i), (ii), (iii), (iv) and/or (v) radicals specified as substituents for the R radicals; or aryl or hetaryl to which may be fused further saturated or unsaturated 5- to 7-membered rings whose carbon skeleton may be interrupted by one or more —O—, —S—, —NR¹, —N=CR¹—, —CR¹=CR¹—, —CO—, —SO— and/or —SO₂— moieties, where the entire ring system may be substituted by the (i), (ii), (iii), (iv) and/or (v) radicals specified as substituents for the R radicals, aryl- and/or hetarylazo, each of which may be substituted by $C_1$-$C_{10}$-alkyl, $C_1$-$C_6$-alkoxy and/or cyano;

each R" is independently hydrogen, $C_1$-$C_{30}$-alkyl, $C_5$-$C_8$-cycloalkyl, aryl or hetaryl or are joined together with formation of a 5- to 7-membered ring which comprises the two oxygen atoms and also the boron atom, to which may be fused unsaturated or saturated rings and which may be substituted on the carbon atoms by up to 4 $C_1$-$C_{30}$-alkyl, $C_5$-$C_8$-cycloalkyl, aryl or hetaryl groups;

R¹ is hydrogen or $C_1$-$C_{18}$-alkyl, where the R¹ radicals may be the same or different when they occur more than once;

R², R³ are each independently hydrogen;

$C_1$-$C_{18}$-alkyl whose carbon chain may be interrupted by one or more —O—, —S—, —CO—, —SO— and/or —SO₂— moieties and which may be mono- or polysubstituted by $C_1$-$C_{12}$-alkoxy, $C_1$-$C_6$-alkylthio, hydroxyl, mercapto, halogen, cyano, nitro and/or —COOR¹;

aryl or hetaryl to each of which may be fused further saturated or unsaturated 5- to 7-membered rings whose carbon skeleton may be interrupted by one or more —O—, —S—, —CO— and/or —SO₂— moieties, where the entire ring system may be mono- or polysubstituted by $C_1$-$C_{12}$-alkyl and/or the above radicals specified as substituents for alkyl;

and where m, m1, n and n1 fulfill at least one of the following conditions:

m=2, m1=1 and n and n1 are integers whose sum adds up to from 0 to 12;

m=2, m1=2 and n and n1 are integers whose sum adds up to from 0 to 16; and (b) cyclodehydrogenating the reaction product obtained in (a) to give a rylene compound of the general formula (I)

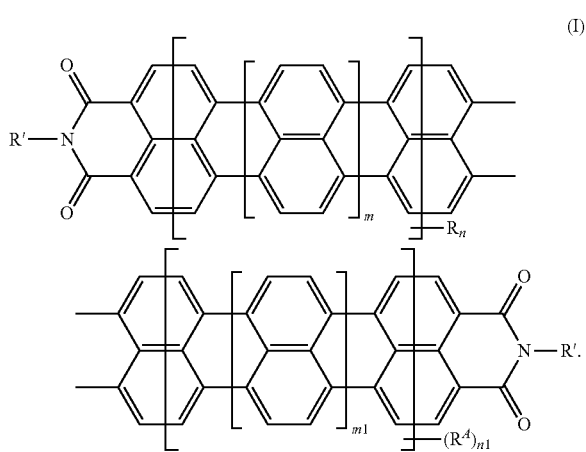

2. A compound of the general formula (I)

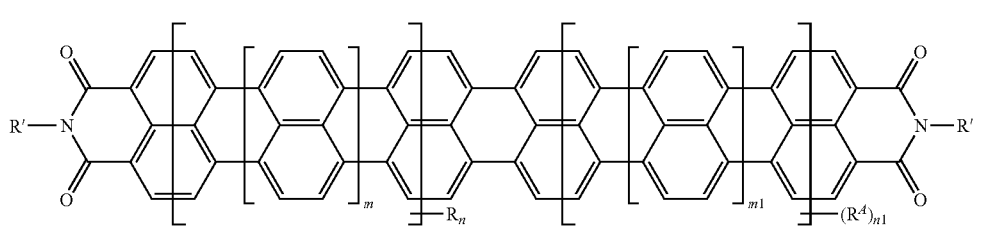

where each R and $R^4$ are independently identical or different radicals selected from the following:

aryloxy, arylthio, hetaryloxy or hetarylthio, to each of which may be fused further saturated or unsaturated 5- to 7-membered rings whose carbon skeleton may be interrupted by one or more —O—, —S—, —NR¹, —N=CR¹—, —CO—, —SO— and/or —SO₂— moieties, where the entire ring system may be mono- or polysubstituted by the (i), (ii), (iii), (iv) and/or (v) radicals:

(i) $C_1$-$C_{30}$-alkyl whose carbon chain may be interrupted by one or more —O—, —S—, —N=CR¹—, —C≡C—, —CR¹=CR¹—, —CO—, —SO— and/or —SO₂— moieties and which may be mono- or polysubstituted by: $C_1$-$C_{12}$-alkoxy, $C_1$-$C_6$-alkylthio, —C≡CR¹, —CR¹=CR¹₂, hydroxyl, mercapto, halogen, cyano, nitro, —NR²R³, —NR²COR³, —CONR²R³, —SO₂NR²R³, —COOR², —SO₃R², —PR²R³, —POR²R³, aryl and/or saturated or unsaturated $C_4$-$C_7$-cycloalkyl whose carbon skeleton may be interrupted by one or more —O—, —S—, —NR$^1$, —N=CR$^1$—, —CR$^1$=CR$^1$—, —CO—, —SO— and/or —SO$_2$— moieties, where the aryl and cycloalkyl radicals may each be mono- or polysubstituted by C$_1$-C$_{18}$-alkyl and/or the above radicals specified as substituents for alkyl;

(ii) C$_3$-C$_8$-cycloalkyl whose carbon skeleton may be interrupted by one or more —O—, —S—, —NR$^1$, —N=CR$^1$—, —CR$^1$=CR$^1$—, —CO—, —SO— and/or —SO$_2$— moieties and to which may be fused further saturated or unsaturated 5- to 7-membered rings whose carbon skeleton may be interrupted by one or more —O—, —S—, —NR$^1$, —N=CR$^1$—, —CR$^1$=CR$^1$—, —CO—, —SO— and/or —SO$_2$-moieties, where the entire ring system may be mono- or polysubstituted by: C$_1$-C$_{18}$-alkyl, C$_1$-C$_{12}$-alkoxy, C$_1$-C$_6$-alkylthio, —C≡CR$^1$, —CR$^1$=CR$^1$$_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, —PR$^2$R$^3$ and/or —POR$^2$R$^3$;

(iii) aryl or hetaryl to which may be fused further saturated or unsaturated 5- to 7-membered rings whose carbon skeleton may be interrupted by one or more —O—, —S—, —N=CR$^1$—, —CR$^1$=CR$^1$—, —CO—, —SO— and/or —SO$_2$— moieties, where the entire ring system may be mono- or polysubstituted by: C$_1$-C$_{18}$-alkyl, C$_1$-C$_{12}$-alkoxy, C$_1$-C$_6$-alkylthio, —CR≡CR$^1$, —CR$^1$=CR$^1$$_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, —PR$^2$R$^3$, —POR$^2$R$^3$, aryl and/or hetaryl, each of which may be substituted by C$_1$-C$_{18}$-alkyl, C$_1$-C$_{12}$-alkoxy, hydroxyl, mercapto, halogen, cyano, nitro, —NR$^2$R$^3$, —NR$^2$COR$^3$, CONR$^2$R$^3$, —SO$_2$NR$^2$R$^3$, —COOR$^2$, —SO$_3$R$^2$, —PR$^2$R$^3$ and/or —POR$^2$R$^3$;

(iv) a —U-aryl radical which may be mono- or polysubstituted by the above radicals specified as substituents for the aryl radicals (iii), where U is a —O—, —S—, NR$^1$, —CO—, —SO— or —SO$_2$— moiety;

(v) C$_1$-C$_{12}$-alkoxy, C$_1$-C$_6$-alkylthio, —C≡CR$^1$, —CR$^1$=CR$^1$$_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, —PR$^2$R$^3$ and/or —POR$^2$R$^3$;

each R' is independently
hydrogen;
C$_1$-C$_{30}$-alkyl whose carbon chain may be interrupted by one or more —O—, —S—, —NR$^1$, —N=CR$^1$—, —C≡C—, —CR$^1$=CR$^1$—, —CO—, —SO— and/or —SO$_2$— moieties and which may be mono- or polysubstituted by the (ii), (iii), (iv) and/or (v) radicals specified as substituents for the R radicals;

C$_3$-C$_8$-cycloalkyl to which may be fused further saturated or unsaturated 5- to 7-membered rings whose carbon skeleton may be interrupted by one or more —O—, —S—, —NR$^1$, —N=CR$^1$—, —CR$^1$=CR$^1$—, —CO—, —SO— and/or —SO$_2$— moieties, where the entire ring system may be substituted by the (i), (ii), (iii), (iv) and/or (v) radicals specified as substituents for the R radicals; or aryl or hetaryl to which may be fused further saturated or unsaturated 5- to 7-membered rings whose carbon skeleton may be interrupted by one or more —O—, —S—, —NR$^1$, —N=CR$^1$—, —CR$^1$=CR$^1$—, —SO— and/or —SO$_2$— moieties, where the entire ring system may be substituted by the (i), (ii), (iii), (iv), (v) radicals specified as substituents for the R radicals, arylazo and/or hetarylazo, each of which may be substituted by C$_1$-C$_{10}$-alkyl, C$_1$-C$_6$-alkoxy and/or cyano;

R$^1$ is hydrogen or C$_1$-C$_{18}$-alkyl, where the R$^1$ radicals may be the same or different when they occur more than once;

R$^2$, R$^3$ are each independently
hydrogen;
C$_1$-C$_{18}$-alkyl whose carbon chain may be interrupted by one or more —O—, —S—, —CO—, —SO— and/or —SO$_2$— moieties and which may be mono- or polysubstituted by C$_1$-C$_{12}$-alkoxy, C$_1$-C$_6$-alkylthio, hydroxyl, mercapto, halogen, cyano, nitro and/or —COOR$^1$;

aryl or hetaryl to each of which may be fused further saturated or unsaturated 5- to 7-membered rings whose carbon skeleton may be interrupted by one or more —O—, —S—, —CO— and/or —SO$_2$— moieties, where the entire ring system may be mono- or polysubstituted by C$_1$-C$_{12}$-alkyl and/or the above radicals specified as substituents for alkyl;

and where m=2, m1=1 and n and n1 are integers whose sum adds up to from 0 to 12.

3. The compound according to claim 2, wherein R and R$^A$ are the same.

4. The compound according to claim 2, wherein R and R$^A$ are each independently aryloxy or arylthio, where the entire ring system may be mono- or polysubstituted by the (i), (ii), (iii), (iv) and/or (v) radicals.

5. The compound according to claim 4, wherein R and R$^A$ may each independently be mono- or polysubstituted by a (i) radical.

6. The compound according to claim 4, wherein R and R$^A$ are each independently

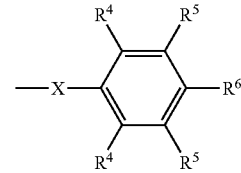

where
X is O or S and
R$^4$, R$^5$ and R$^6$ may each independently be hydrogen or the (i), (ii), (iii), (iv) and/or (v) radicals, with the proviso that at least one of the R$^4$ and R$^6$ radicals is not hydrogen.

7. The compound according to claim 6, wherein, when R$^4$ is C$_1$-C$_{30}$-alkyl or C$_3$-C$_8$-cycloalkyl, a ternary carbon atom does not occur in a 1-position relative to the phenyl group to which R$^4$ is attached.

8. The compound according to claim 6, wherein neither R$^4$ is hydrogen and R$^5$ and R$^6$ are each hydrogen, or R$^6$ is not hydrogen and R$^4$ and R$^5$ are each hydrogen.

9. The compound according to claim 2, wherein each R' is independently C$_1$-C$_{30}$-alkyl or aryl, where the entire ring system may be mono- or polysubstituted by the (i), (ii), (iii), (iv) and/or (v) radicals.

10. The compound according to claim 9, wherein R' is mono- or polysubstituted by a (i) radical.

11. A method of using a compound according to claim 2 for coloring high molecular weight organic and inorganic materials, as dispersing assistants and pigment additives for organic pigments, for preparing aqueous polymer dispersions which absorb in the near infrared region of the electromagnetic spectrum, for obtaining markings and inscriptions which absorb infrared light and are invisible to the human eye, as infrared absorbers for heat management, as IR laser beam-absorbing materials in the fusion treatment of plastics parts, as semiconductors in organic electronics, as emitters in electro- and chemiluminescence applications, or as active components in photovoltaics.

12. A compound of the general formula (I)

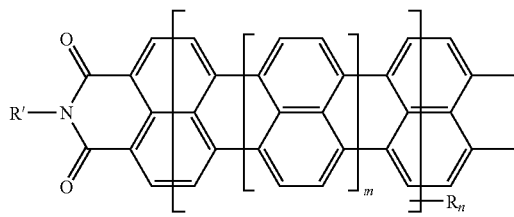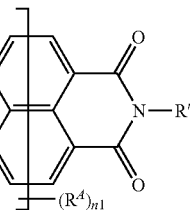

(I)

where
each $R$, $R^4$ are independently identical or different radicals selected from the following:

aryloxy, arylthio, hetaryloxy or hetarylthio, to each of which may be fused further saturated or unsaturated 5- to 7-membered rings whose carbon skeleton may be interrupted by one or more —O—, —S—, —NR$^1$, —N=CR$^1$—, —CO—, —SO— and/or —SO$_2$— moieties, where the entire ring system may be mono- or polysubstituted by the (i), (ii), (iii), (iv) and/or (v) radicals:

(i) $C_1$-$C_{30}$-alkyl whose carbon chain may be interrupted by one or more —O—, —S—, —N=CR$^1$—, —C≡C—, —CR$^1$=CR$^1$—, —CO—, —SO— and/or —SO$_2$— moieties and which may be mono- or polysubstituted by: $C_1$-$C_{12}$-alkoxy, $C_1$-$C_6$-alkylthio, —C≡CR$^1$, —CR$^1$=CR$^1{}_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, —PR$^2$R$^3$, —POR$^2$R$^3$, aryl and/or saturated or unsaturated $C_4$-$C_7$-cycloalkyl whose carbon skeleton may be interrupted by one or more —O—, —S—, —NR$^1$, —N=CR$^1$—, —CR$^1$=CR$^1$—, —CO—, —SO— and/or —SO$_2$— moieties, where the aryl and cycloalkyl radicals may each be mono- or polysubstituted by $C_1$-$C_{18}$-alkyl and/or the above radicals specified as substituents for alkyl;

(ii) $C_3$-$C_8$-cycloalkyl whose carbon skeleton may be interrupted by one or more —O—, —S—, —NR$^1$, —N=CR$^1$—, —CR$^1$=CR$^1$—, —CO—, —SO— and/or —SO$_2$— moieties and to which may be fused further saturated or unsaturated 5- to 7-membered rings whose carbon skeleton may be interrupted by one or more —O—, —S—, —NR$^1$, —N=CR$^1$—, —CR$^1$=CR$^1$—, —CO—, —SO— and/or —SO$_2$-moieties, where the entire ring system may be mono- or polysubstituted by: $C_1$-$C_{18}$-alkyl, $C_1$-$C_{12}$-alkoxy, $C_1$-$C_6$-alkylthio, —C≡CR$^1$, —CR$^1$=CR$^1{}_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, —PR$^2$R$^3$ and/or —POR$^2$R$^3$;

(iii) aryl or hetaryl to which may be fused further saturated or unsaturated 5- to 7-membered rings whose carbon skeleton may be interrupted by one or more —O—, —S—, —N=CR$^1$—, —CR$^1$=CR$^1$—, —CO—, —SO— and/or —SO$_2$— moieties, where the entire ring system may be mono- or polysubstituted by: $C_1$-$C_{18}$-alkyl, $C_1$-$C_{12}$-alkoxy, $C_1$-$C_6$-alkylthio, —CR≡CR$^1$, —CR$^1$=CR$^1{}_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, —PR$^2$R$^3$, —POR$^2$R$^3$, aryl and/or hetaryl, each of which may be substituted by $C_1$-$C_{18}$-alkyl, $C_1$-$C_{12}$-alkoxy, hydroxyl, mercapto, halogen, cyano, nitro, —NR$^2$R$^3$, —NR$^2$COR$^3$, CONR$^2$R$^3$, —SO$_2$NR$^2$R$^3$, —COOR$^2$, —SO$_3$R$^2$, —PR$^2$R$^3$ and/or —POR$^2$R$^3$;

(iv) a —U-aryl radical which may be mono- or polysubstituted by the above radicals specified as substituents for the aryl radicals (iii), where U is a —O—, —S—, NR$^1$, —CO—, —SO— or —SO$_2$— moiety;

(v) $C_1$-$C_{12}$-alkoxy, $C_1$-$C_6$-alkylthio, —C≡CR$^1$, —CR$^1$=CR$^1{}_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, —PR$^2$R$^3$ and/or —POR$^2$R$^3$;

each R' is independently
hydrogen;
$C_1$-$C_{30}$-alkyl whose carbon chain may be interrupted by one or more —O—, —S—, —NR$^1$, —N=CR$^1$—, —C≡C—, —CR$^1$=CR$^1$—, —CO—, —SO— and/or —SO$_2$— moieties and which may be mono- or polysubstituted by the (ii), (iii), (iv) and/or (v) radicals specified as substituents for the R radicals;
$C_3$-$C_8$-cycloalkyl to which may be fused further saturated or unsaturated 5- to 7-membered rings whose carbon skeleton may be interrupted by one or more —O—, —S—, —NR$^1$, —N=CR$^1$—, —CR$^1$=CR$^1$—, —CO—, —SO— and/or —SO$_2$— moieties, where the entire ring system may be substituted by the (i), (ii), (iii), (iv) and/or (v) radicals specified as substituents for the R radicals; or
aryl or hetaryl to which may be fused further saturated or unsaturated 5- to 7-membered rings whose carbon skeleton may be interrupted by one or more —O—, —S—, —NR$^1$, —N=CR$^1$—, —CR$^1$=CR$^1$—, —CO—, —SO— and/or —SO$_2$— moieties, where the entire ring system may be substituted by the (i), (ii), (iii), (iv), (v) radicals specified as substituents for the R radicals, aryl- and/or hetarylazo, each of which may be substituted by $C_1$-$C_{10}$-alkyl, $C_1$-$C_6$-alkoxy and/or cyano;

$R^1$ is hydrogen or $C_1$-$C_{18}$-alkyl, where the $R^1$ radicals may be the same or different when they occur more than once;

$R^2$, $R^3$ are each independently
hydrogen;
$C_1$-$C_{18}$-alkyl whose carbon chain may be interrupted by one or more —O—, —S—, —CO—, —SO— and/or —SO$_2$— moieties and which may be mono- or polysubstituted by $C_1$-$C_{12}$-alkoxy, $C_1$-$C_6$-alkylthio, hydroxyl, mercapto, halogen, cyano, nitro and/or —COOR$^1$;
aryl or hetaryl to each of which may be fused further saturated or unsaturated 5- to 7-membered rings whose carbon skeleton may be interrupted by one or more —O—, —S—, —CO— and/or —SO$_2$— moieties, where the entire ring system may be mono- or polysubstituted by C$_1$-C$_{12}$-alkyl and/or the above radicals specified as substituents for alkyl;

and where m=2, m1=2 and n and n1 are integers whose sum adds up to from 0 to 16.

13. The compound according to claim 12, wherein R and R$^A$ are the same.

14. The compound according to claim 12, wherein R and R$^A$ are each independently aryloxy or arylthio, where the entire ring system may be mono- or polysubstituted by the (i), (ii), (iii), (iv) and/or (v) radicals.

15. The compound according to claim 14, wherein R and R$^A$ may each independently be mono- or polysubstituted by a (i) radical.

16. The compound according to claim 14, wherein R and R$^A$ are each independently

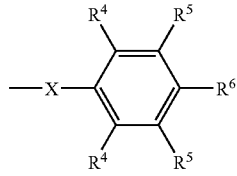

where

X is O or S and

R$^4$, R$^5$ and R$^6$ may each independently be hydrogen or the (i), (ii), (iii), (iv) and/or (v) radicals, with the proviso that at least one of the R$^4$ and R$^6$ radicals is not hydrogen.

17. The compound according to claim 16, wherein, when R$^4$ is C$_1$-C$_{30}$-alkyl or C$_3$-C$_8$-cycloalkyl, a ternary carbon atom does not occur in a 1-position relative to the phenyl group to which R$^4$ is attached.

18. The compound according to claim 16, wherein neither R$^4$ is hydrogen and R$^5$ and R$^6$ are each hydrogen, or R$^6$ is not hydrogen and R$^4$ and R$^5$ are each hydrogen.

19. The compound according to claim 12, wherein each R' is independently C$_1$-C$_{30}$-alkyl or aryl, where the entire ring system may be mono- or polysubstituted by the (i), (ii), (iii), (iv) and/or (v) radicals.

20. The compound according to claim 19, wherein R' is mono- or poly-substituted by a (i) radical.

21. A method of using a compound according to claim 12 for coloring high molecular weight organic and inorganic materials, as dispersing assistants and pigment additives for organic pigments, for preparing aqueous polymer dispersions which absorb in the near infrared region of the electromagnetic spectrum, for obtaining markings and inscriptions which absorb infrared light and are invisible to the human eye, as infrared absorbers for heat management, as IR laser beam-absorbing materials in the fusion treatment of plastics parts, as semiconductors in organic electronics, as emitters in electro- and chemiluminescence applications, or as active components in photovoltaics.

22. A process for preparing a compound of the general formula (II)

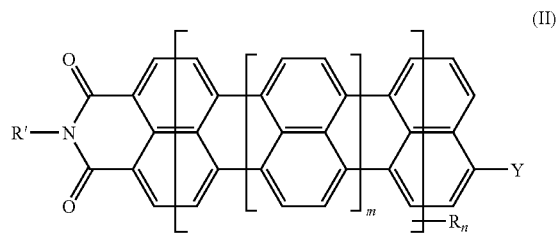

where

Y is halogen;

R is selected from the following: aryloxy, arylthio, hetaryloxy or hetarylthio, to each of which may be fused further saturated or unsaturated 5- to 7-membered rings whose carbon skeleton may be interrupted by one or more —O—, —S—, —NR$^1$, —N=CR$^1$—, —CO—, —SO— and/or —SO$_2$-moieties, where the entire ring system may be mono- or polysubstituted by the (i), (ii), (iii), (iv) and/or (v) radicals;

(i) C$_1$-C$_{30}$-alkyl whose carbon chain may be interrupted by one or more —O—, —S—, NR$^1$, —N=CR$^1$—, —C≡CR$^1$=CR$^1$—, —CO—, —SO— and/or —SO$_2$— moieties and which may be mono- or polysubstituted by: C$_1$-C$_{12}$-alkoxy, C$_1$-C$_6$-alkylthio, —C≡CR$^1$, —CR$^1$=CR$^1$$_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, —PR$^2$R$^3$, —POR$^2$R$^3$, aryl and/or saturated or unsaturated C$_4$-C$_7$-cycloalkyl whose carbon skeleton may be interrupted by one or more —O—, —S—, —NR$^1$, —N=CR$^1$—, —CR$^1$=CR$^1$—, —CO—, —SO— and/or —SO$_2$— moieties, where the aryl and cycloalkyl radicals may each be mono- or polysubstituted by C$_1$-C$_{18}$-alkyl and/or the above radicals specified as substituents for alkyl;

(ii) C$_3$-C$_8$-cycloalkyl whose carbon skeleton may be interrupted by one or more —O—, —S—, —NR$^1$, —N=CR$^1$—, —CR$^1$=CR$^1$—, —CO—, —SO— and/or —SO$_2$— moieties and to which may be fused further saturated or unsaturated 5- to 7-membered rings whose carbon skeleton may be interrupted by one or more —O—, —S—, —NR$^1$, —N=CR$^1$—, —CR$^1$=CR$^1$—, —CO—, —SO— and/or —SO$_2$-moieties, where the entire ring system may be mono- or polysubstituted by: C$_1$-C$_{18}$-alkyl, C$_1$-C$_{12}$-alkoxy, C$_1$-C$_6$-alkylthio, —C≡CR$^1$=CR$^1$$_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, —PR$^2$R$^3$ and/or —POR$^2$R$^3$;

(iii) aryl or hetaryl to which may be fused further saturated or unsaturated 5- to 7-membered rings whose carbon skeleton may be interrupted by one or more —O—, —S—, —N=CR$^1$—, —CR$^1$=CR$^1$—, —CO—, —SO— and/or —SO$_2$— moieties, where the entire ring system may be mono- or polysubstituted by: C$_1$-C$_{18}$-alkyl, C$_1$-C$_{12}$-alkoxy, C$_1$-C$_6$-alkylthio, —CR≡CR$^1$, —CR$^1$=CR$^1$$_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, —PR$^2$R$^3$, —POR$^2$R$^3$, aryl and/or hetaryl, each of which may be substituted by C$_1$-C$_{18}$-alkyl, C$_1$-C$_{12}$-alkoxy, hydroxyl, mercapto, halogen, cyano, nitro, —NR$^2$R$^3$, —NR$^2$COR$^3$, CONR$^2$R$^3$, —SO$_2$NR$^2$R$^3$, —COOR$^2$, —SO$_3$R$^2$, —PR$^2$R$^3$ and/or —POR$^2$R$^3$;

(iv) a —U-aryl radical which may be mono- or polysubstituted by the above radicals specified as substituents for the aryl radicals (iii), where U is a —O—, —S—, NR$^1$, —CO—, —SO— or —SO$_2$— moiety;

(v) $C_1$-$C_{12}$-alkoxy, $C_1$-$C_6$-alkylthio, —C≡CR$^1$=CR$^1_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, —PR$^2$R$^3$ and/or —POR$^2$R$^3$;

each R' is independently hydrogen;

$C_1$-$C_{30}$-alkyl whose carbon chain may be interrupted by one or more —O—, —S—, —NR$^1$, —N=CR$^1$—, —C≡C—, —CR$^1$=CR$^1$—, —CO—, —SO— and/or —SO$_2$— moieties and which may be mono- or polysubstituted by the (ii), (iii), (iv) and/or (v) radicals specified as substituents for the R radicals;

$C_3$-$C_8$-cycloalkyl to which may be fused further saturated or unsaturated 5- to 7-membered rings whose carbon skeleton may be interrupted by one or more —O—, —S—, —NR$^1$, —N=CR$^1$—, —CR$^1$=CR$^1$—, —CO—, —SO— and/or —SO$_2$— moieties, where the entire ring system may be substituted by the (i), (ii), (iii), (iv) and/or (v) radicals specified as substituents for the R radicals; or aryl or hetaryl to which may be fused further saturated or unsaturated 5- to 7-membered rings whose carbon skeleton may be interrupted by one or more —O—, —S—, —NR$^1$, —N=CR$^1$—, —CR$^1$=CR$^1$—, —CO—, —SO— and/or —SO$_2$— moieties, where the entire ring system may be substituted by the (i), (ii), (iii), (iv), (v) radicals specified as substituents for the R radicals, aryl- and/or hetarylazo, each of which may be substituted by $C_1$-$C_{10}$-alkyl, $C_1$-$C_6$-alkoxy and/or cyano;

R$^1$ is hydrogen or $C_1$-$C_{18}$-alkyl, where the R$^1$ radicals may be the same or different when they occur more than once;

R$^2$, R$^3$ are each independently hydrogen;

$C_1$-$C_{18}$-alkyl whose carbon chain may be interrupted by one or more —O—, —S—, —CO—, —SO— and/or —SO$_2$— moieties and which may be mono- or polysubstituted by $C_1$-$C_{12}$-alkoxy, $C_1$-$C_6$-alkylthio, hydroxyl, mercapto, halogen, cyano, nitro and/or —COOR$^1$;

aryl or hetaryl to each of which may be fused further saturated or unsaturated 5- to 7-membered rings whose carbon skeleton may be interrupted by one or more —O—, —S—, —CO—and/or —SO$_2$— moieties, where the entire ring system may be mono- or polysubstituted by $C_1$-$C_{12}$-alkyl and/or the above radicals specified as substituents for alkyl;

and where m is 2; and n is an integer from 0 to 16, comprising (a) coupling at least one perylene compound of the formula (II)

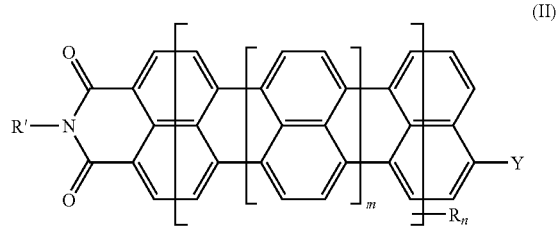

with at least one compound of the formula (IIIa) and/or (IIIa')

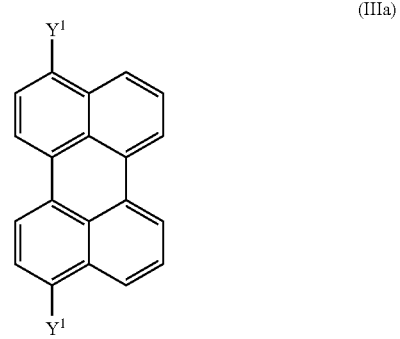

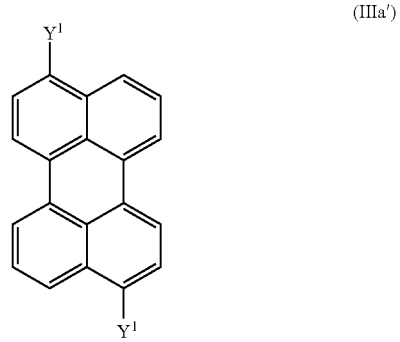

where one radical of Y and Y$^1$ is halogen and the other is B(OR'')$_2$, m=0, and R, R$^1$ and n are each as defined above to give a compound of the general formula (IIIb)/(IIIb')

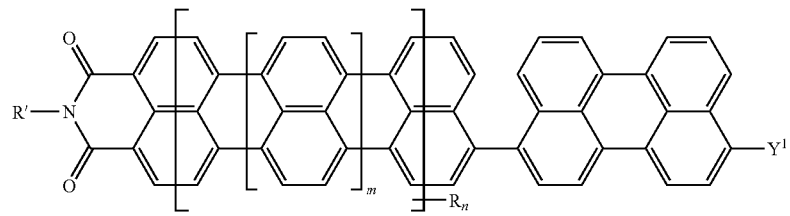

-continued

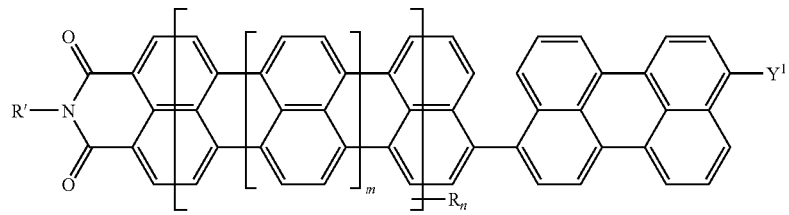

(IIIb')

where each R" is independently hydrogen, $C_1$-$C_{30}$-alkyl, $C_5$-$C_8$-cycloalkyl, aryl or hetaryl or are joined together with formation of a 5- to 7-membered ring which comprises the two oxygen atoms and also the boron atom, to which may be fused unsaturated or saturated rings and which may be substituted on the carbon atoms by up to 4 $C_1$-$C_{30}$-alkyl, $C_5$-$C_8$-cycloalkyl, aryl or hetaryl groups and (b) cyclodehydrogenating the compound of the general formula (IIIb)/(IIIb') obtained in (a) to give a rylene compound of the general formula (II), where $Y^1$ in formula (IIIb)/(IIIb') is as defined for Y in formula (II).

23. A compound of the general formula (IIIb) or (IIIb')

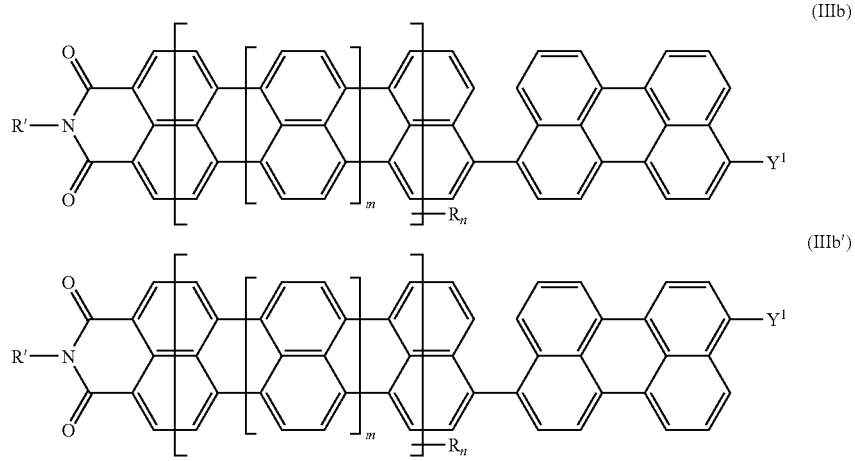

(IIIb)

(IIIb')

where
R is selected from the following:
aryloxy, arylthio, hetaryloxy or hetarylthio, to each of which may be fused further saturated or unsaturated 5- to 7-membered rings whose carbon skeleton may be interrupted by one or more —O—, —S—, —$NR^1$—, —N=$CR^1$—, —CO—, —SO— and/or —$SO_2$— moieties, where the entire ring system may be mono- or polysubstituted by the (i), (ii), (iii), (iv) and/or (v) radicals:

(i) $C_1$-$C_{30}$-alkyl whose carbon chain may be interrupted by one or more —O—, —S—, —$NR^1$—, —N=$CR^1$—, C=C—, —$CR^1$=$CR^1$—, —CO—, —SO— and/or —$SO_2$— moieties and which may be mono- or polysubstituted by: $C_1$-$C_{12}$-alkoxy, $C_1$-$C_6$-alkylthio, —C=$CR^1$, —$CR^1$=$CR^1{}_2$, hydroxyl, mercapto, halogen, cyano, nitro, —$NR^2R^3$, —$NR^2COR^3$, —$CONR^2R^3$, —$SO_2NR^2R^3$, —$COOR^2$, —$SO_3R^2$, —$PR^2R^3$, —$POR^2R^3$, aryl and/or saturated or unsaturated $C_4$-$C_7$— cycloalkyl whose carbon skeleton may be interrupted by one or more —O—, —S—, —$NR^1$, —N=$CR^1$—, —$CR^1$=$CR^1$—, —CO—, —SO— and/or —$SO_2$— moieties, where the aryl and cycloalkyl radicals may each be mono- or polysubstituted by $C_1$-$C_{18}$-alkyl and/or the above radicals specified as substituents for alkyl;

(ii) $C_3$-$C_8$-cycloalkyl whose carbon skeleton may be interrupted by one or more —O—, —S—, —$NR^1$—, —N=$CR^1$—, —$CR^1$=$CR^1$—, —CO—, —SO— and/or —$SO_2$— moieties and to which may be fused further saturated or unsaturated 5- to 7-membered rings whose carbon skeleton may be interrupted by one or more —O—, —S—, —$NR^1$, —N=$CR^1$—, —$CR^1$=$CR^1$—, —CO—, —SO— and/or —$SO_2$-moieties, where the entire ring system may be mono- or polysubstituted by: $C_1$-$C_{18}$-alkyl, $C_1$-$C_{12}$-alkoxy, $C_1$-$C_6$-alkylthio, —C=$CR^1$, —$CR^1$=$CR^1{}_2$, hydroxyl, mercapto, halogen, cyano, nitro, —$NR^2R^3$, —$NR^2COR^3$, —$CONR^2R^3$, —$SO_2NR^2R^3$, —$COOR^2$, —$SO_3R^2$, —$PR^2R^3$ and/or —$POR^2R^3$;

(iii) aryl or hetaryl to which may be fused further saturated or unsaturated 5- to 7-membered rings whose carbon skeleton may be interrupted by one or more —O—, —S—, —$NR^1$, —N=$CR^1$—, —$CR^1$=$CR^1$—, —CO—, —SO— and/or —$SO_2$— moieties, where the entire ring system may be mono- or polysubstituted by: $C_1$-$C_{18}$-alkyl, $C_1$-$C_{12}$-alkoxy, $C_1$-$C_6$-alkylthio, —C=$CR^1$, —$CR^1$=$CR^1{}_2$, hydroxyl, mercapto, halogen, cyano, nitro, —$NR^2R^3$, —$NR^2COR^3$, —$CONR^2R^3$, —$SO_2NR^2R^3$, —$COOR^2$, —$SO_3 1 3^2$, —$PR^2R^3$, —$POR^2R^3$, aryl and/or hetaryl, each of which may be substituted by $C_1$-$C_{18}$-alkyl, $C_1$-$C_{12}$-alkoxy, hydroxyl, mercapto, halogen, cyano, nitro, —$NR^2R^3$, —$NR^2COR^3$, —$CONR^2R^3$, —$SO_2NR^2R^3$, —$COOR^2$, —$SO_3R^2$, —$PR^2R^3$ and/or —$POR^2R^3$;

(iv) a —U-aryl radical which may be mono- or polysubstituted by the above radicals specified as substituents for the aryl radicals (iii), where U is a —O—, —S—, —$NR^{1-}$, —CO—, —SO— or —$SO_2$— moiety;

(v) $C_1$-$C_{12}$-alkoxy, $C_1$-$C_6$-alkylthio, —C=$CR^1$, —$CR^1$=$CR^1_2$, hydroxyl, mercapto, halogen, cyano, nitro, —$NR^2R^3$, —$NR^2COR^3$, —$CONR^2R^3$, —$SO_2NR^2R^3$, —$COOR^2$, —$SO_3R^2$, —$PR^2R^3$ and/or —$POR^2R^3$;

each $R^1$ is independently hydrogen;

$C_1$-$C_{30}$-alkyl whose carbon chain may be interrupted by one or more —O—, —S—, —$NR^1$, —N=$CR^1$—, —C≡C—, —$CR^1$=$CR^1$—, —CO—, —SO— and/or —$SO_2$— moieties and which may be mono- or polysubstituted by the (ii), (iii), (iv) and/or (v) radicals specified as substituents for the R radicals;

$C_3$-$C_8$-cycloalkyl to which may be fused further saturated or unsaturated 5- to 7-membered rings whose carbon skeleton may be interrupted by one or more —O—, —S—, —$NR^1$, —N=$CR^1$—, —$CR^1$=$CR^1$—, —CO—, —SO— and/or —$SO_2$— moieties, where the entire ring system may be substituted by the (i), (ii), (iii), (iv) and/or (v) radicals specified as substituents for the R radicals; or aryl or hetaryl to which may be fused further saturated or unsaturated 5- to 7-membered rings whose carbon skeleton may be interrupted by one or more —O—, —S—, —$NR^1$, —N=$CR^1$—, —$CR^1$=$CR^1$—, —CO—, —SO— and/or —$SO_2$— moieties, where the entire ring system may be substituted by the (i), (ii), (iii), (iv), (v) radicals specified as substituents for the R radicals, arylazo and/or hetarylazo, each of which may be substituted by $C_1$-$C_{10}$-alkyl, $C_1$-$C_6$-alkoxy and/or cyano;

$R^1$ is hydrogen or $C_1$-$C_{18}$-alkyl, where the $R^1$ radicals may be the same or different when they occur more than once;

$R^2$, $R^3$ are each independently hydrogen;

$C_1$-$C_{18}$-alkyl whose carbon chain may be interrupted by one or more —O—, —S—, —CO—, —SO— and/or —$SO_2$— moieties and which may be mono- or polysubstituted by $C_1$-$C_{12}$-alkoxy, $C_1$-$C_6$-alkylthio, hydroxyl, mercapto, halogen, cyano, nitro and/or —$COOR^1$;

aryl or hetaryl to each of which may be fused further saturated or unsaturated 5- to 7-membered rings whose carbon skeleton may be interrupted by one or more —O—, —S—, —CO— and/or —$SO_2$— moieties, where the entire ring system may be mono- or polysubstituted by $C_1$-$C_{12}$-alkyl and/or the above radicals specified as substituents for alkyl;

m is 0;

n is an integer from 0 to 16; and $Y^1$ is halogen or B(OR") where each R" is independently hydrogen, $C_1$-$C_{30}$-alkyl, $C_5$-$C_8$-cycloalkyl, aryl or hetaryl or are joined together with formation of a 5- to 7-membered ring which comprises the two oxygen atoms and also the boron atom, to which may be fused unsaturated or saturated rings and which may be substituted on the carbon atoms by up to 4 $C_1$-$C_{30}$-alkyl, $C_5$-$C_8$-cycloalkyl, aryl or hetaryl groups.

24. A compound according to claim 23, which is a compound of the general formula (IIIb).

25. A compound according to claim 23, which is a compound of the general formula (IIIb').

\* \* \* \* \*